US012642460B2

(12) United States Patent
Marriott et al.

(10) Patent No.: US 12,642,460 B2
(45) Date of Patent: Jun. 2, 2026

(54) VITAL SIGNS OR HEALTH MONITORING SYSTEMS AND METHODS

(71) Applicant: RDS, Strasbourg (FR)

(72) Inventors: Mark P. Marriott, Palo Alto, CA (US); Jeffrey C. Marshall, Belmont, CA (US); George Stefan Golda, El Granada, CA (US); Sam Eletr, Paris (FR)

(73) Assignee: RDS, Strasbourg (FR)

( * ) Notice: Subject to any disclaimer, the term of this patent is extended or adjusted under 35 U.S.C. 154(b) by 660 days.

(21) Appl. No.: 17/922,215

(22) PCT Filed: Apr. 29, 2021

(86) PCT No.: PCT/EP2021/061250
§ 371 (c)(1),
(2) Date: Oct. 28, 2022

(87) PCT Pub. No.: WO2021/219779
PCT Pub. Date: Nov. 4, 2021

(65) Prior Publication Data
US 2023/0172499 A1 Jun. 8, 2023

Related U.S. Application Data

(60) Provisional application No. 63/138,264, filed on Jan. 15, 2021, provisional application No. 63/059,966, (Continued)

(51) Int. Cl.
*A61B 5/024* (2006.01)
*A61B 5/00* (2006.01)
(Continued)

(52) U.S. Cl.
CPC ........ *A61B 5/14552* (2013.01); *A61B 5/0006* (2013.01); *A61B 5/02416* (2013.01);
(Continued)

(58) Field of Classification Search
CPC .............. A61B 5/1455; A61B 5/14551; A61B 5/14552
See application file for complete search history.

(56) References Cited

U.S. PATENT DOCUMENTS 3,769,669 A 11/1973 Peacock et al.
3,830,970 A 8/1974 Hurley et al.
(Continued)

FOREIGN PATENT DOCUMENTS

CN 2785556 Y 6/2006
CN 101822533 A 9/2010
(Continued)

OTHER PUBLICATIONS

Partial European Search Report for Application No. 19194996.5 issued by the European Patent Office, Feb. 6, 2020, 15 pages, EPO, Munich, Germany.
(Continued)

*Primary Examiner* — Daniel L Cerioni
(74) *Attorney, Agent, or Firm* — EIP US LLP

(57) ABSTRACT

The present disclosure relates to a pulse oximetry method in which the contribution of venous capillaries to photoplethys-mogram is reduced below 25%.

15 Claims, 20 Drawing Sheets

Related U.S. Application Data filed on Jul. 31, 2020, provisional application No. 63/017,595, filed on Apr. 29, 2020.

(51) Int. Cl.
| | |
|---|---|
| *A61B 5/1455* | (2006.01) |
| *A61B 5/352* | (2021.01) |
| *A61B 5/366* | (2021.01) |

(52) U.S. Cl.
CPC .............. *A61B 5/352* (2021.01); *A61B 5/366* (2021.01); *A61B 5/6833* (2013.01)

(56) References Cited

U.S. PATENT DOCUMENTS

| | | |
|---|---|---|
| 3,911,906 A | 10/1975 | Reinhold, Jr. |
| 4,141,366 A | 2/1979 | Cross, Jr. et al. |
| 4,164,215 A | 8/1979 | Finlayson et al. |
| 4,221,223 A | 9/1980 | Linden |
| 4,224,948 A | 9/1980 | Cramer |
| 4,230,127 A | 10/1980 | Larson |
| 4,295,472 A | 10/1981 | Adams |
| 4,360,030 A | 11/1982 | Citron et al. |
| 4,412,546 A | 11/1983 | Barthels |
| 4,494,550 A | 1/1985 | Blazek et al. |
| 4,580,339 A | 4/1986 | Ioffe |
| 4,583,190 A | 4/1986 | Salb |
| 4,583,549 A | 4/1986 | Manoli |
| 4,674,511 A | 6/1987 | Cartmell |
| 4,803,992 A | 2/1989 | Lemelson |
| 4,859,057 A | 8/1989 | Taylor et al. |
| 4,869,254 A | 9/1989 | Stone et al. |
| 4,880,304 A | 11/1989 | Jaeb et al. |
| 4,890,622 A | 1/1990 | Ferrari |
| 4,902,886 A | 2/1990 | Smisko |
| 4,934,372 A | 6/1990 | Corenman et al. |
| 4,938,228 A | 7/1990 | Righter et al. |
| 4,967,264 A | 10/1990 | Parulski et al. |
| 5,025,791 A | 6/1991 | Niwa |
| 5,184,620 A | 2/1993 | Cudahy et al. |
| 5,203,329 A | 4/1993 | Takatani et al. |
| 5,215,087 A | 6/1993 | Anderson |
| 5,224,486 A | 7/1993 | Lerman et al. |
| 5,261,401 A | 11/1993 | Baker et al. |
| 5,265,579 A | 11/1993 | Ferrari |
| 5,307,818 A | 5/1994 | Segalowitz |
| 5,372,125 A | 12/1994 | Lyons |
| 5,419,321 A | 5/1995 | Evans |
| 5,427,093 A | 6/1995 | Ogawa et al. |
| 5,448,991 A | 9/1995 | Polson et al. |
| 5,465,715 A | 11/1995 | Lyons |
| 5,465,727 A | 11/1995 | Reinhold |
| 5,511,553 A | 4/1996 | Segalowitz |
| 5,549,116 A | 8/1996 | Mauer |
| 5,632,272 A | 5/1997 | Diab et al. |
| 5,673,692 A | 10/1997 | Schulze et al. |
| 5,730,143 A | 3/1998 | Schwarzberg |
| 5,779,631 A | 7/1998 | Chance |
| 5,817,008 A | 10/1998 | Rafert et al. |
| 5,912,703 A | 6/1999 | Tamayama |
| 5,931,791 A | 8/1999 | Saltzstein et al. |
| 5,938,597 A | 8/1999 | Stratbucker |
| 5,971,930 A | 10/1999 | Elghazzawi |
| 5,995,373 A | 11/1999 | Nagai |
| 6,032,060 A | 2/2000 | Carim et al. |
| 6,041,247 A | 3/2000 | Weckstrom et al. |
| 6,088,607 A | 7/2000 | Diab et al. |
| 6,122,535 A | 9/2000 | Kastle et al. |
| 6,134,460 A | 10/2000 | Chance |
| 6,263,222 B1 | 7/2001 | Diab et al. |
| 6,327,487 B1 | 12/2001 | Stratbucker |
| 6,385,473 B1 | 5/2002 | Haines et al. |
| 6,453,186 B1 | 9/2002 | Lovejoy et al. |
| 6,525,386 B1 | 2/2003 | Mills et al. |
| 6,526,300 B1 | 2/2003 | Kiani et al. |
| 6,569,095 B2 | 5/2003 | Eggers |
| 6,647,287 B1 | 11/2003 | Peel et al. |
| 6,661,161 B1 | 12/2003 | Lanzo |
| 6,662,033 B2 | 12/2003 | Casciani et al. |
| 6,665,385 B2 | 12/2003 | Rogers et al. |
| 6,694,177 B2 | 2/2004 | Eggers et al. |
| 6,699,194 B1 | 3/2004 | Diab et al. |
| 6,725,074 B1 | 4/2004 | Kastle |
| 6,745,061 B1 | 6/2004 | Hicks et al. |
| 6,801,137 B2 | 10/2004 | Eggers |
| 6,830,711 B2 | 12/2004 | Mills et al. |
| 6,934,570 B2 | 8/2005 | Kiani et al. |
| 6,940,403 B2 | 9/2005 | Kail, IV |
| 7,018,338 B2 | 3/2006 | Vetter et al. |
| 7,027,858 B2 | 4/2006 | Cao et al. |
| 7,067,893 B2 | 6/2006 | Mills et al. |
| 7,099,715 B2 | 8/2006 | Korzinov et al. |
| 7,130,396 B2 | 10/2006 | Rogers et al. |
| 7,194,300 B2 | 3/2007 | Korzinov |
| 7,212,850 B2 | 5/2007 | Prystowsky |
| 7,215,984 B2 | 5/2007 | Diab et al. |
| 7,257,438 B2 | 8/2007 | Kinast |
| 7,332,784 B2 | 2/2008 | Mills et al. |
| 7,341,559 B2 | 3/2008 | Schulz et al. |
| 7,412,282 B2 | 8/2008 | Houben |
| 7,502,643 B2 | 3/2009 | Farringdon et al. |
| 7,553,166 B2 | 6/2009 | Gobron |
| 7,587,237 B2 | 9/2009 | Korzinov et al. |
| 7,668,588 B2 | 2/2010 | Kovacs |
| 7,729,753 B2 | 6/2010 | Kremliovsky et al. |
| 7,831,301 B2 | 11/2010 | Webb et al. |
| 7,881,765 B2 | 2/2011 | Mertz et al. |
| D634,431 S | 3/2011 | Severe et al. |
| 7,904,133 B2 | 3/2011 | Gehman et al. |
| 7,907,996 B2 | 3/2011 | Prystowsky et al. |
| 7,941,207 B2 | 5/2011 | Korzinov |
| 7,962,202 B2 | 6/2011 | Bhunia |
| 7,988,638 B2 | 8/2011 | Novae |
| 8,116,841 B2 | 2/2012 | Bly et al. |
| 8,145,287 B2 | 3/2012 | Diab et al. |
| 8,150,502 B2 | 4/2012 | Kumar et al. |
| 8,160,682 B2 | 4/2012 | Kumar et al. |
| D659,836 S | 5/2012 | Bensch et al. |
| 8,172,761 B1 | 5/2012 | Rulkov et al. |
| 8,200,319 B2 | 6/2012 | Pu et al. |
| 8,200,320 B2 | 6/2012 | Kovacs |
| 8,203,704 B2 | 6/2012 | Merritt et al. |
| 8,219,198 B2 | 7/2012 | Gollasch et al. |
| 8,249,686 B2 | 8/2012 | Libbus et al. |
| 8,271,072 B2 | 9/2012 | Houben et al. |
| RE43,767 E | 10/2012 | Eggers et al. |
| 8,285,356 B2 | 10/2012 | Bly et al. |
| 8,290,129 B2 | 10/2012 | Rogers et al. |
| 8,290,574 B2 | 10/2012 | Feild et al. |
| 8,301,236 B2 | 10/2012 | Baumann et al. |
| 8,374,686 B2 | 2/2013 | Ghanem |
| 8,428,682 B1 | 4/2013 | Rood et al. |
| 8,452,364 B2 | 5/2013 | Hannula et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,538,503 B2 | 9/2013 | Kumar et al. |
| 8,554,311 B2 | 10/2013 | Warmer et al. |
| 8,560,046 B2 | 10/2013 | Kumar et al. |
| 8,577,431 B2 | 11/2013 | Lamego et al. |
| 8,585,605 B2 | 11/2013 | Sola I Caros et al. |
| 8,591,430 B2 | 11/2013 | Amurthur et al. |
| D701,964 S | 4/2014 | Yoneta et al. |
| 8,688,190 B2 | 4/2014 | Libbus et al. |
| 8,718,752 B2 | 5/2014 | Libbus et al. |
| 8,731,649 B2 | 5/2014 | Lisogurski |
| 8,743,258 B2 | 6/2014 | Park et al. |
| 8,821,397 B2 | 9/2014 | Al-Ali et al. |
| 8,989,830 B2 | 3/2015 | LeBoeuf et al. |
| D738,757 S | 9/2015 | Gross et al. |
| D744,109 S | 11/2015 | Yoneta et al. |
| D744,110 S | 11/2015 | Kubo et al. |
| 9,186,112 B2 | 11/2015 | Bechtel et al. |
| 9,241,643 B2 | 1/2016 | Lisogurski |

(56) References Cited

U.S. PATENT DOCUMENTS

| | | | |
|---|---|---|---|
| 9,277,864 B2 | 3/2016 | Yang et al. |
| 9,289,175 B2 | 3/2016 | LeBoeuf et al. |
| D760,903 S | 7/2016 | Lin et al. |
| 9,392,946 B1 | 7/2016 | Sarantos |
| 9,398,870 B2 | 7/2016 | Bechtel et al. |
| 9,506,802 B2 | 11/2016 | Chu et al. |
| D787,066 S | 5/2017 | Kim et al. |
| 9,636,057 B2 | 5/2017 | Scheuing et al. |
| 9,642,565 B2 | 5/2017 | Gonopolskiy et al. |
| 9,664,556 B2 | 5/2017 | Chu et al. |
| 9,696,199 B2 | 7/2017 | Chu et al. |
| 9,717,425 B2 | 8/2017 | Kiani et al. |
| 9,752,925 B2 | 9/2017 | Chu et al. |
| D800,313 S | 10/2017 | Chang |
| 9,775,548 B2 | 10/2017 | Sarantos et al. |
| 9,782,132 B2 | 10/2017 | Golda et al. |
| 9,801,547 B2 | 10/2017 | Yuen et al. |
| D810,944 S | 2/2018 | Goolkasian |
| 9,888,872 B2 | 2/2018 | Bechtel et al. |
| D812,229 S | 3/2018 | Al-Siddiq |
| 10,045,722 B2 | 8/2018 | Kintz et al. |
| 10,080,527 B2 | 9/2018 | Golda et al. |
| 10,088,356 B2 | 10/2018 | Chu et al. |
| 10,244,949 B2 | 4/2019 | Moyer et al. |
| D850,626 S | 6/2019 | Gardner et al. |
| D851,253 S | 6/2019 | Goolkasian |
| 10,413,251 B2 | 9/2019 | Golda et al. |
| D868,974 S | 12/2019 | Albert et al. |
| D868,977 S | 12/2019 | Vardi |
| D880,703 S | 4/2020 | Emery et al. |
| 10,610,159 B2 | 4/2020 | Eletr et al. |
| 10,824,391 B2 | 11/2020 | Savolainen et al. |
| 10,842,391 B2 | 11/2020 | Moyer et al. |
| 10,863,947 B2 | 12/2020 | Golda et al. |
| 10,959,678 B2 | 3/2021 | Golda et al. |
| 10,980,486 B2 | 4/2021 | Van Zandt Moyer et al. |
| D931,467 S | 9/2021 | Golda et al. |
| 11,185,291 B2 | 11/2021 | Eletr et al. |
| 2002/0026127 A1 | 2/2002 | Balbierz et al. |
| 2002/0038082 A1 | 3/2002 | Chin |
| 2002/0072685 A1 | 6/2002 | Rymut et al. |
| 2002/0180605 A1 | 12/2002 | Ozguz et al. |
| 2003/0055478 A1 | 3/2003 | Lyster et al. |
| 2003/0065269 A1 | 4/2003 | Vetter et al. |
| 2003/0073916 A1 | 4/2003 | Yonce |
| 2003/0139654 A1 | 7/2003 | Kim et al. |
| 2003/0149349 A1 | 8/2003 | Jensen |
| 2003/0176795 A1 | 9/2003 | Harris et al. |
| 2003/0225322 A1 | 12/2003 | Uchiyama et al. |
| 2003/0225323 A1 | 12/2003 | Kani et al. |
| 2004/0010201 A1 | 1/2004 | Korzinov et al. |
| 2004/0015091 A1 | 1/2004 | Greenwald et al. |
| 2004/0019288 A1 | 1/2004 | Kinast |
| 2004/0039419 A1 | 2/2004 | Stickney et al. |
| 2004/0039420 A1 | 2/2004 | Jayne et al. |
| 2004/0042581 A1 | 3/2004 | Okerlund et al. |
| 2004/0054273 A1 | 3/2004 | Finneran et al. |
| 2004/0082842 A1 | 4/2004 | Lumba et al. |
| 2004/0082862 A1 | 4/2004 | Chance |
| 2004/0146149 A1 | 7/2004 | Rogers et al. |
| 2004/0260189 A1 | 12/2004 | Eggers et al. |
| 2005/0096557 A1 | 5/2005 | Vosburgh et al. |
| 2005/0187446 A1 | 8/2005 | Nordstrom et al. |
| 2005/0197549 A1 | 9/2005 | Baker, Jr. |
| 2005/0197793 A1 | 9/2005 | Baker, Jr. |
| 2005/0261559 A1 | 11/2005 | Mumford et al. |
| 2005/0277841 A1 | 12/2005 | Shennib |
| 2005/0288726 A1 | 12/2005 | Gollasch |
| 2006/0056487 A1 | 3/2006 | Kuroda et al. |
| 2006/0079792 A1 | 4/2006 | Finburgh et al. |
| 2006/0167515 A1 | 7/2006 | Stickney et al. |
| 2006/0170649 A1 | 8/2006 | Kosugi et al. |
| 2006/0224072 A1 | 10/2006 | Shennib |
| 2007/0032719 A1 | 2/2007 | Menon et al. |
| 2007/0070800 A1 | 3/2007 | Virag et al. |
| 2007/0093705 A1 | 4/2007 | Shin et al. |
| 2007/0103296 A1 | 5/2007 | Paessel et al. |
| 2007/0106136 A1 | 5/2007 | Sterling et al. |
| 2007/0129642 A1 | 6/2007 | Korzinov |
| 2007/0130657 A1 | 6/2007 | Rogers et al. |
| 2007/0142715 A1 | 6/2007 | Banet et al. |
| 2007/0156054 A1 | 7/2007 | Korzinov |
| 2007/0167850 A1 | 7/2007 | Russell et al. |
| 2007/0191723 A1 | 8/2007 | Prystowsky et al. |
| 2007/0191728 A1 | 8/2007 | Shennib |
| 2007/0206655 A1 | 9/2007 | Haslett et al. |
| 2007/0208542 A1 | 9/2007 | Vock et al. |
| 2007/0255156 A1 | 11/2007 | Mertz et al. |
| 2007/0255184 A1 | 11/2007 | Shennnib |
| 2007/0282212 A1 | 12/2007 | Sierra et al. |
| 2007/0293776 A1 | 12/2007 | Korzinov et al. |
| 2008/0013747 A1 | 1/2008 | Tran |
| 2008/0061846 A1 | 3/2008 | Kase et al. |
| 2008/0091090 A1 | 4/2008 | Guillory et al. |
| 2008/0101064 A1 | 5/2008 | Draganov et al. |
| 2008/0139953 A1 | 6/2008 | Baker et al. |
| 2008/0288026 A1 | 11/2008 | Cross et al. |
| 2008/0294126 A1 | 11/2008 | Reuben |
| 2008/0300641 A1 | 12/2008 | Brunekreeft et al. |
| 2009/0054742 A1 | 2/2009 | Kaminska et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0105602 A1 | 4/2009 | Gehman et al. |
| 2009/0171177 A1 | 7/2009 | Hannula et al. |
| 2009/0234410 A1 | 9/2009 | Libbus et al. |
| 2009/0290279 A1 | 11/2009 | Rodgriguez et al. |
| 2009/0306536 A1 | 12/2009 | Ranganathan et al. |
| 2010/0004518 A1 | 1/2010 | Vo et al. |
| 2010/0026995 A1 | 2/2010 | Merritt et al. |
| 2010/0030039 A1 | 2/2010 | Lamego et al. |
| 2010/0054138 A1 | 3/2010 | Gips et al. |
| 2010/0134241 A1 | 6/2010 | Gips et al. |
| 2010/0160794 A1 | 6/2010 | Banet et al. |
| 2010/0179391 A1 | 7/2010 | Quintanar et al. |
| 2010/0191509 A1 | 7/2010 | Li et al. |
| 2010/0198044 A1 | 8/2010 | Gehman et al. |
| 2010/0204586 A1 | 8/2010 | Pu et al. |
| 2010/0204599 A1 | 8/2010 | Pu et al. |
| 2010/0249541 A1 | 9/2010 | Geva et al. |
| 2010/0262430 A1 | 10/2010 | Gips et al. |
| 2010/0268103 A1 | 10/2010 | Mcnamara et al. |
| 2010/0286495 A1 | 11/2010 | McGonigle et al. |
| 2010/0286532 A1 | 11/2010 | Farringdon et al. |
| 2010/0298655 A1 | 11/2010 | McCombie et al. |
| 2010/0298656 A1 | 11/2010 | McCombie et al. |
| 2010/0312188 A1 | 12/2010 | Robertson et al. |
| 2010/0317937 A1 | 12/2010 | Kuhn et al. |
| 2010/0317942 A1 | 12/2010 | Cinbis et al. |
| 2010/0317947 A1 | 12/2010 | Cinbis et al. |
| 2010/0317958 A1 | 12/2010 | Beck et al. |
| 2010/0318146 A1 | 12/2010 | Cinbis et al. |
| 2010/0324387 A1 | 12/2010 | Moon et al. |
| 2010/0324389 A1 | 12/2010 | Moon et al. |
| 2011/0004106 A1 | 1/2011 | Iwamiya et al. |
| 2011/0021897 A1 | 1/2011 | Webb et al. |
| 2011/0066039 A1 | 3/2011 | Banet et al. |
| 2011/0066049 A1 | 3/2011 | Matsumoto et al. |
| 2011/0066062 A1 | 3/2011 | Banet et al. |
| 2011/0098933 A1 | 4/2011 | Ochs |
| 2011/0105860 A1 | 5/2011 | Houben et al. |
| 2011/0105926 A1 | 5/2011 | Kornet |
| 2011/0112421 A1 | 5/2011 | Zanetti |

(56) References Cited

U.S. PATENT DOCUMENTS

| | | |
|---|---|---|
| 2011/0124979 A1 | 5/2011 | Heneghan |
| 2011/0125040 A1 | 5/2011 | Crawford et al. |
| 2011/0144470 A1 | 6/2011 | Mazar et al. |
| 2011/0158284 A1 | 6/2011 | Goto |
| 2011/0160604 A1 | 6/2011 | Istvan et al. |
| 2011/0166434 A1 | 7/2011 | Gargiulo |
| 2011/0166468 A1 | 7/2011 | Prystowsky et al. |
| 2011/0190598 A1 | 8/2011 | Shusterman |
| 2011/0194007 A1 | 8/2011 | Kim et al. |
| 2011/0208076 A1 | 8/2011 | Fong et al. |
| 2011/0208078 A1 | 8/2011 | Cho et al. |
| 2011/0263994 A1 | 10/2011 | Burns et al. |
| 2011/0270049 A1 | 11/2011 | Katra et al. |
| 2011/0270112 A1 | 11/2011 | Manera et al. |
| 2011/0279963 A1 | 11/2011 | Kumar |
| 2011/0301445 A9 | 12/2011 | Webb et al. |
| 2011/0301493 A1 | 12/2011 | Husheer |
| 2012/0016245 A1 | 1/2012 | Niwa et al. |
| 2012/0029306 A1 | 2/2012 | Paquet et al. |
| 2012/0029320 A1 | 2/2012 | Watson et al. |
| 2012/0035490 A1 | 2/2012 | Shen et al. |
| 2012/0035494 A1 | 2/2012 | Chakravarthy et al. |
| 2012/0061695 A1 | 3/2012 | Kim |
| 2012/0071744 A1 | 3/2012 | Euliano et al. |
| 2012/0083673 A1 | 4/2012 | Al-Ali et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0109572 A1 | 5/2012 | Shimizu |
| 2012/0110226 A1 | 5/2012 | Mach et al. |
| 2012/0110228 A1 | 5/2012 | Mach et al. |
| 2012/0136226 A1 | 5/2012 | Wilke |
| 2012/0143079 A1 | 6/2012 | Lia et al. |
| 2012/0176599 A1 | 7/2012 | Leung et al. |
| 2012/0179011 A1 | 7/2012 | Moon et al. |
| 2012/0197150 A1 | 8/2012 | Cao et al. |
| 2012/0203077 A1 | 8/2012 | He et al. |
| 2012/0204068 A1 | 8/2012 | Ye et al. |
| 2012/0226129 A1 | 9/2012 | Callahan et al. |
| 2012/0232369 A1 | 9/2012 | Kim et al. |
| 2012/0245951 A1 | 9/2012 | Gips et al. |
| 2012/0277549 A1 | 11/2012 | Libbus et al. |
| 2012/0284003 A1 | 11/2012 | Gosh |
| 2012/0289839 A1 | 11/2012 | Takenoshita et al. |
| 2012/0330126 A1 | 12/2012 | Hoppe et al. |
| 2012/0330151 A1 | 12/2012 | Weinstein et al. |
| 2013/0012938 A1 | 1/2013 | Asirvatham et al. |
| 2013/0030257 A1 | 1/2013 | Nakata et al. |
| 2013/0030259 A1 | 1/2013 | Thomsen et al. |
| 2013/0085347 A1 | 4/2013 | Manicka et al. |
| 2013/0085708 A1 | 4/2013 | Sattler |
| 2013/0096395 A1 | 4/2013 | Katra et al. |
| 2013/0116520 A1 | 5/2013 | Roham et al. |
| 2013/0116534 A1 | 5/2013 | Woo |
| 2013/0116585 A1 | 5/2013 | Bouguerra |
| 2013/0144130 A1 | 6/2013 | Russell et al. |
| 2013/0158372 A1 | 6/2013 | Haisley et al. |
| 2013/0172691 A1 | 7/2013 | Tran |
| 2013/0172724 A1 | 7/2013 | Aziz et al. |
| 2013/0225938 A1 | 8/2013 | Vlach |
| 2013/0225967 A1 | 8/2013 | Esposito |
| 2013/0245388 A1 | 9/2013 | Rafferty et al. |
| 2013/0245394 A1 | 9/2013 | Brown et al. |
| 2013/0245415 A1 | 9/2013 | Kumar et al. |
| 2013/0253285 A1 | 9/2013 | Bly et al. |
| 2013/0261422 A1 | 10/2013 | Gilmore et al. |
| 2013/0267854 A1 | 10/2013 | Johnson et al. |
| 2013/0296660 A1 | 11/2013 | Tsien et al. |
| 2013/0296823 A1 | 11/2013 | Melker et al. |
| 2013/0324812 A1 | 12/2013 | Brainard |
| 2013/0324816 A1 | 12/2013 | Bechtel et al. |
| 2013/0324855 A1 | 12/2013 | Lisogurski et al. |
| 2013/0324856 A1 | 12/2013 | Lisogurski et al. |
| 2013/0331665 A1 | 12/2013 | Libbus et al. |
| 2013/0338448 A1 | 12/2013 | Libbus et al. |
| 2013/0338460 A1 | 12/2013 | He et al. |
| 2014/0038147 A1 | 2/2014 | Morrow |
| 2014/0066726 A1 | 3/2014 | Costello |
| 2014/0066732 A1 | 3/2014 | Addison et al. |
| 2014/0066783 A1 | 3/2014 | Kiani et al. |
| 2014/0081152 A1 | 3/2014 | Clinton |
| 2014/0091926 A1 | 4/2014 | Gips et al. |
| 2014/0100432 A1 | 4/2014 | Golda et al. |
| 2014/0121557 A1 | 5/2014 | Gannon et al. |
| 2014/0206976 A1 | 7/2014 | Thompson et al. |
| 2014/0228656 A1 | 8/2014 | Gonopolskiy et al. |
| 2014/0275869 A1 | 9/2014 | Kintz et al. |
| 2014/0276089 A1 | 9/2014 | Kirenko et al. |
| 2015/0057511 A1 | 2/2015 | Basu |
| 2015/0087948 A1 | 3/2015 | Bishay et al. |
| 2015/0087951 A1 | 3/2015 | Felix et al. |
| 2015/0094551 A1 | 4/2015 | Frix et al. |
| 2015/0094552 A1 | 4/2015 | Golda et al. |
| 2015/0148622 A1 | 5/2015 | Moyer et al. |
| 2015/0148637 A1 | 5/2015 | Golda et al. |
| 2015/0148691 A1 | 5/2015 | Moyer et al. |
| 2015/0335288 A1 | 11/2015 | Toth et al. |
| 2015/0351690 A1 | 12/2015 | Toth et al. |
| 2016/0073954 A1 | 3/2016 | Meitav |
| 2016/0238440 A1 | 8/2016 | Chu et al. |
| 2016/0302674 A1 | 10/2016 | Moyer et al. |
| 2016/0345844 A1* | 12/2016 | McCombie ........ A61B 5/02125 |
| 2016/0345881 A1 | 12/2016 | Sarantos et al. |
| 2017/0027513 A1 | 2/2017 | Mulpuru |
| 2017/0095156 A1 | 4/2017 | Richards |
| 2017/0337412 A1 | 11/2017 | Bhat et al. |
| 2017/0337413 A1 | 11/2017 | Bhat et al. |
| 2018/0028122 A1 | 2/2018 | Golda et al. |
| 2018/0085068 A1 | 3/2018 | Telfort |
| 2018/0092443 A1 | 4/2018 | Albers et al. |
| 2018/0177459 A1 | 6/2018 | Eletr et al. |
| 2018/0199882 A1* | 7/2018 | Klee .................... A61B 5/4818 |
| 2018/0235473 A1* | 8/2018 | Meftah ............. A61B 5/02416 |
| 2018/0242876 A1 | 8/2018 | Hughes et al. |
| 2018/0325385 A1 | 11/2018 | Deterding et al. |
| 2019/0029599 A1 | 1/2019 | Golda et al. |
| 2019/0282096 A1 | 9/2019 | Vardi |
| 2019/0320914 A1 | 10/2019 | Moyer et al. |
| 2020/0008749 A1 | 1/2020 | Golda et al. |
| 2020/0221974 A1* | 7/2020 | Singh ................... A61B 5/4561 |
| 2020/0229767 A1 | 7/2020 | Eletr et al. |
| 2020/0237309 A1 | 7/2020 | Golda et al. |
| 2021/0059586 A1 | 3/2021 | Marriott et al. |
| 2021/0100514 A1 | 4/2021 | Golda et al. |
| 2021/0145293 A1 | 5/2021 | Van Zandt Moyer et al. |
| 2021/0212638 A1 | 7/2021 | Golda et al. |
| 2021/0236064 A1 | 8/2021 | Van Zandt Moyer et al. |
| 2022/0142495 A1* | 5/2022 | De Marco ............ A61B 5/0261 |

FOREIGN PATENT DOCUMENTS

| | | |
|---|---|---|
| CN | 201641985 U | 11/2010 |
| CN | 101984743 A | 3/2011 |
| CN | 102215747 A | 10/2011 |
| CN | 202288274 U | 7/2012 |
| CN | 105997103 A | 10/2016 |
| CN | 104812296 B | 5/2018 |
| EP | 0581073 A2 | 2/1994 |
| EP | 1737337 B1 | 5/2005 |
| EP | 1139858 B1 | 4/2007 |
| EP | 2438851 A2 | 4/2012 |
| EP | 2305103 B1 | 9/2013 |
| EP | 3099224 A1 | 12/2016 |
| EP | 2903509 B1 | 9/2019 |
| EP | 3636148 A1 | 4/2020 |
| EP | 3099224 B1 | 5/2020 |
| EP | 3636148 A3 | 5/2020 |
| EP | 3769669 A1 | 1/2021 |
| JP | 52-052494 | 4/1977 |
| JP | 02172443 A | 7/1990 |
| JP | H05123305 A | 5/1993 |
| JP | H07213630 A | 8/1995 |
| JP | H09224917 A | 9/1997 |
| JP | 2001029318 A | 2/2001 |

(56) References Cited

FOREIGN PATENT DOCUMENTS

| | | | |
|---|---|---|---|
| JP | 2001078974 | A | 3/2001 |
| JP | 2002125944 | A | 5/2002 |
| JP | 2002263075 | A | 9/2002 |
| JP | 2004000474 | | 1/2004 |
| JP | 2004016248 | A | 1/2004 |
| JP | 2006000481 | A | 1/2006 |
| JP | 2006158813 | A | 6/2006 |
| JP | 3952082 | B2 | 8/2007 |
| JP | 2007244531 | A | 9/2007 |
| JP | 2007296266 | A | 11/2007 |
| JP | 2011-147746 | | 8/2011 |
| JP | 20120187404 | A | 10/2012 |
| JP | 5408751 | B2 | 2/2014 |
| JP | 6298063 | B2 | 3/2018 |
| JP | 6539827 | B2 | 7/2019 |
| JP | 6625682 | B2 | 12/2019 |
| JP | 2020513876 | A | 5/2020 |
| WO | W09401039 | A1 | 1/1994 |
| WO | WO9427494 | A1 | 12/1994 |
| WO | WO0045696 | A1 | 8/2000 |
| WO | WO0059374 | A1 | 10/2000 |
| WO | WO01/043624 | A4 | 6/2001 |
| WO | WO2001085019 | A2 | 11/2001 |
| WO | WO2001093758 | A1 | 12/2001 |
| WO | W00200094 | A2 | 1/2002 |
| WO | WO2002085201 | A1 | 10/2002 |
| WO | WO2002086792 | A2 | 10/2002 |
| WO | WO2002086835 | A1 | 10/2002 |
| WO | WO2002086837 | A1 | 10/2002 |
| WO | WO2003077752 | A1 | 9/2003 |
| WO | WO2005079429 | A2 | 1/2005 |
| WO | WO2005060829 | A1 | 7/2005 |
| WO | WO2005072237 | A2 | 8/2005 |
| WO | W02006014806 | A2 | 2/2006 |
| WO | WO2006044919 | A2 | 4/2006 |
| WO | WO2006110488 | A2 | 10/2006 |
| WO | W02006124788 | A2 | 11/2006 |
| WO | WO2006124788 | A2 | 11/2006 |
| WO | 2008092098 | A2 | 7/2008 |
| WO | WO2008092098 | A3 | 10/2008 |
| WO | WO2009036321 | A1 | 3/2009 |
| WO | WO2009036327 | A1 | 3/2009 |
| WO | 2009112972 | A2 | 9/2009 |
| WO | WO2010/055155 | A2 | 5/2010 |
| WO | WO2010093900 | A2 | 8/2010 |
| WO | WO2010104952 | A2 | 9/2010 |
| WO | WO2010107913 | A2 | 9/2010 |
| WO | W02011074004 | A2 | 6/2011 |
| WO | WO2012104658 | A2 | 8/2012 |
| WO | WO2012129498 | A1 | 9/2012 |
| WO | WO2012150563 | A1 | 11/2012 |
| WO | 2014027293 | A2 | 2/2014 |
| WO | 2014027293 | A3 | 2/2014 |
| WO | 2014055994 | A1 | 4/2014 |
| WO | 2015113054 | A1 | 7/2015 |
| WO | WO2015120330 | A1 | 8/2015 |
| WO | WO2013/071014 | A2 | 5/2016 |
| WO | 2016210334 | A1 | 12/2016 |
| WO | WO2018112401 | A1 | 6/2018 |
| WO | 2020154697 | A1 | 7/2020 |

OTHER PUBLICATIONS

International Search Report and Written Opinion of the International Searching Authority. International Application No. PCT/EP2021/061250 issued by the European Patent Office, mail date Jul. 15, 2021, 11 pages, EPO, P.B. 5818 Patentlaan 2, Rijswijk, NL 2280.

Extended European Search Report including the Supplementary European Search Report for Application No. EP15740972 issued by the European Patent Office, Munich, Germany dated Aug. 29, 2017.

Transmittal of Copy of International Preliminary Report of Patentability and International Preliminary Report on Patentability for Application No. PCT/US2016/039374 issued by the International Bureau of WIPO, Geneva, Switzerland date of mailing Jan. 4, 2018 which includes: The International Preliminary Report on Patentability date of issuance Dec. 26, 2017 with Written Opinion of the International Searching Authority for International Application No. PCT/US2016/039374 mail date Oct. 28, 2016 issued by the United States Patent Office.

Extended European Search Report for Application No. EP19194996 issued by the European Patent Office, dated Apr. 22, 2020, 18 pages, EPO, Munich, Germany.

Palreddy, Surekha, Chapter 9—Signal Processing Algorithms, Design of Pulse Oximeters, Medical Science Series, Bristol [U.A.]; Institute of Physics Pub, GB, Jan. 1, 1997, pp. 124-158, 133-157, Taylor & Francis Group, LLC., New York, NY and Milton Park, Abingdon, Oxon, England.

International Search Report and Written Opinion of the International Searching Authority. International Application No. PCT/US20/15099 issued by the United State Patent Office, mail date Jun. 4, 2020, 11 pages, Alexandria Virginia.

Yoo, Jerald et al., A 5.2 mW Self-Configured Wearable Body Sensor Network controller and a 12 uW Wirelessly Powered Sensor for a Continuous Health Monitoring System, IEEE Journal of Solid-State Circuits, Jan. 2010, pp. 178-188, vol. 45, Issue No. 1, Institute of Electrical and Electronics Engineers, Piscataway, NJ.

International Search Report and Written Opinion of the International Searching Authority. International Application No. PCT/US2013/063748 issued by the United State Patent Office, mail date Feb. 27, 2014, 15 pages, Alexandria Virginia.

Timmerman, Luke, Xconomy, Inc., "UW Spinout Cardiac Insight Wins FDA OK for Heartbeat Monitor", published Jun. 6, 2013; website accessed Oct. 27, 2013, http://www.xconomy.com/seattle/2013/06/06/uw-spinout-cardiac-insight-wins-fda-ok-for-heartbeat-monitor/, Xconomy Inc., Cambridge, Massachusetts.

CardioNet, Inc., "CardioNet, Inc. Announces Launch of MCOTos 2:1 Device", published Jun. 19, 2013; website accessed Oct. 27, 2013, https://www.cardionet.com/index.htm, BioTelemetry, Inc., Conshohocken, Pennsylvania.

Heart Check, "The HeartCheck Pen, a Handheld ECG with SMART Monitoring", website accessed Oct. 27, 2013, http://heartcheckpen.com/, HeartCheckPEN.com, TAW Global, LLC, Portage, Michigan; CardioComm Solutions Inc., Toronto, ON, and Victoria, BC.

Corventis, Inc., "Nuvant Mobile Cardiac Telemetry", Copyright 2009-2013; website accessed Oct. 27, 2013, http://corventis.com/, Corventis, San Jose, California.

Transmittal of Copy of International Preliminary Report on Patentability mailing date of Apr. 16, 2015 and International Preliminary Report on Patentability date of issuance of report Apr. 7, 2015 with Written Opinion of the International Searching Authority International Application No. PCT/US2013/063748 issued by the United State Patent Office, mail date Feb. 27, 2014, 5 pages, Alexandria, Virginia.

International Search Report and Written Opinion of the International Searching Authority. International Application No. PCT/US2015/13113 issued by the United State Patent Office, mail date Jun. 29, 2015, 14 pages, Alexandria Virginia.

European Supplementary Search Report dated Aug. 8, 2022 for European Application No. EP 20 74 5511.

United States Final Office Action dated Jul. 21, 2023 for U.S. Appl. No. 16/752,554.

United States Final Office Action dated Nov. 22, 2023 for U.S. Appl. No. 17/234,133.

Notification of transmittal of the International Search Report and the Written Opinion of the International SearchingAuthority for Application No. PCT/US2017/066805 issued by the International Searching Authority, Alexandria, VA date of mailing Mar. 12, 2018, 1 page, which includes: The International Search Report completed Feb. 7, 2018 mail date Mar. 12, 2018, 5 pages, with Written Opinion of the International Searching Authority for International Application No. PCT/US2017/066805 mail date Mar. 12, 2018 issued by the United States Patent Office, Alexandria,.

International Search Report and Written Opinion of the International Searching Authority. International Application No. PCT/

(56) References Cited

OTHER PUBLICATIONS

US2016/039374 issued by the United State Patent Office, mail date Oct. 28, 2016, 14 pages, Alexandria Virginia. (needs to be cited 101, 201, 301, 401, 701).

Supplementary European Search Report for Application No. EP17880188 issued by the European Patent Office, Aug. 5, 2020, 8 pages, EPO, Munich, Germany.

Extended European Search Report for Application No. EP20175192 issued by the European Patent Office, dated Oct. 26, 2020, 12 pages, EPO, Munich, Germany.

International Search Report and Written Opinion of the International Searching Authority. International Application No. PCT/US2020/048603 issued by the United States Patent Office, mail date Jan. 4, 2020, 18 pages, USPTO, Alexandria, Virginia, USA.

Allen, John, Photoplethysmography and its application in clinical physiological measurement, Physiological Measurement, Feb. 20, 2007, pp. R1-R39, vol. 28, No. 3, IOP Publishing Ltd., Bristol, United Kingdom.

Supplementary European Search Report for Application No.

EP16815429 issued by the European Patent Office, Jan. 17, 2019, 4 pages, EPO, Munich, Germany.

PDF "Dictionary_composite" from https://www.merriam-webster.com/dictionary/composite accessed on Feb. 12, 2019 (Year:2019).

Extended European Search Report including the Supplementary European Search Report (SESR) for Application No. EP13843561.5 issued by the European Patent Office, Munich, Germany dated Apr. 29, 2016.

Kansy, Robert J., Response of a Correlated Double Sampling Circuity to 1/f Noise, IEEE Journal of Solid-State Circuits, Jun. 1980, pp. 373-375, vol. SC-15, No. 3, IEEE, New York, NY, USA.

Japanese Office Action dated/transmitted Aug. 31, 2021 for Japanese Application No. 2019531741—original and translation.

Chinese Office Action, Application No. 201780077645.7, Jun. 15, 2021, China National Intellectual Property Administration, Beijing, China.

Kadota, Hiroshi, Japanese Patent Office, Japanese Office Action dated/transmitted Nov. 30, 2021 for Japanese Application No. 2020-218861, original 3 pages, and translation 3 pages; Japanese Patent Office.

* cited by examiner

250

250

251

Red Pulse 0          10          20          30

252

Red Pulse 10          0          10          20          30

DETERMINE FRAME BOUNDARIES — 620

ADD SAMPLE VALUES AT CORRESPONDING TIME POINTS OF EACH FRAMGE FOR IR AND RED SIGNALS — 622

DETERMINE AVERAGE VALUES FOR CORRESPONDING TIME POINTS OF EACH FRAME — 624

COMPUTE OXYGEN SATURATION FROM AVERAGE VALUES — 626

1

VITAL SIGNS OR HEALTH MONITORING SYSTEMS AND METHODS

FIELD OF INVENTION

The present disclosure relates to a pulse oximetry method using a photoplethysmography sensor placed on the body of a patient. The contribution of venous capillaries to the measured photoplethysmogram is lower than 25%. This low contribution of venous capillaries may be obtained either by placing the photoplethysmography sensor in a specific location of the patient—for instance on the back—or by processing photoplethysmogram with another signal acquired in time concordance—for instance an ECG signal.

BACKGROUND OF INVENTION

Advances in software, electronics, sensor technology and materials science have revolutionized patient monitoring technologies. In particular, many devices and systems are becoming available for a variety of vital signs or health monitoring applications. However, improvements may yet be desired for vital signs or health monitoring devices and systems that provide one or more of effective data collection and/or manipulation for parameter determination. In particular, usual methods to determine pulse oximetry are based on acquisition of photoplethysmograms in reflectance. However, signal collected by photoplethysmography sensor is a sum of an arterial contribution, periodic and allowing for SpO2 determination, and a venous contribution superposed randomly to arterial contribution, thus lowering accuracy of SpO2 determination. This phenomenon is well known as "venous shift".

Further alternatives for patients and their physicians may then be developed to include robust and convenient monitors that in some instances may collect and transfer short-term or long-term data and/or monitor events in real-time, or substantial real-time, and in some cases may include multivariable parameter determination.

In this disclosure, methods to get rid of "venous shift" have been identified in the general context of vital signs and health monitoring systems and methods.

SUMMARY

Described herein are several alternative medical monitoring devices, systems and/or methods for parameter determination, in some instances for long-term sensing and/or recording of cardiac and/or respiratory data of one or more individuals, such as a neonate, infant, mother/parent, athlete, or patient. A number of alternative implementations and applications are summarized and/or exemplified herein below and throughout this specification. In particular, pulse oximetry methods are herein described.

In one alternative aspect, the developments hereof may include an implementation wherein a health device is configured for monitoring one or a plurality of physiological parameters of one or more individuals from time-concordant measurements collected by one or a plurality of sensors, including one or a variety of one or more of, but not limited to, electrodes for measuring ionic potential changes for electrocardiograms (ECGs), and/or one or more light sources and one or more photodetectors, in some cases including LED-photodiode pairs or groupings, for optically based oxygen saturation measurements.

In another alternative aspect hereof, a blood pressure determination may in some cases be made from a determination of pulse transit time. The pulse transit time is the time for the cardiac pressure wave to travel from the heart to other locations in the body. Measurements of pulse transit time may then be used to estimate blood pressure. Heart beat timing from ECG or otherwise and photoplethysmogram (aka PPG) signals can be used to generate pulse transit time. Note, such signals may be generated from conventional or other to-be-developed processes and/or devices or systems; or, such signals may be taken from one or more wearable health monitoring devices such as those also described hereinbelow.

In another alternative aspect, the developments hereof may include in some instances one or more methods and/or devices for measuring and/or determining oxygen saturation parameters from time concordant pulse oximetry signals and ECG signals. In some implementations, ECG signals may be used to define intervals, or "frames" of pulse oximetry data that are collected and averaged for determining the constant and main periodic components (e.g., DC and AC components) of the pulse oximetry signals from which, in turn, values for oxygen saturation may be determined. Patient-wearable devices of such implementations with pulse oximetry and ECG sensors may be particularly useful when placed on a patient's chest or alternatively on a patient's back for such signal acquisition.

This disclosure thus relates to a pulse oximetry method comprising:

Placing a photoplethysmography sensor on the body of a patient;

Determining a photoplethysmogram with contribution of venous capillaries lower than 25%, preferably lower than 15%, more preferably lower than 10%;

Determining arterial pulses in photoplethysmogram; and

Determining peripheral oxygen saturation using Ratio of Ratios method.

In a first variant, determining a photoplethysmogram with contribution of venous capillaries lower than 25% comprises:

Determining an electrocardiogram in time concordance with photoplethysmogram;

Detecting the QRS complex of successive heart beats in said electrocardiogram;

Defining a succession of frames of photoplethysmogram for a time interval between two adjacent heart beats; and Aggregating two or more of these frames together at each point in time to create a photoplethysmogram for the time interval in which contribution of venous capillaries is lower than 25%, preferably lower than 15%, more preferably lower than 10%.

In an embodiment of the first variant, the pulse oximetry method further comprises Determining Pulse Transit Time from time concordant electrocardiogram and photoplethysmogram for each heart beat;

Computing standard deviation of Pulse Transit Time over a period comprising between 10 and 45 heart beats; and Determining a confidence level of peripheral oxygen saturation determination from standard deviation of Pulse Transit Time.

In an embodiment of the first variant, two or more photoplethysmography waveforms of different wavelength are determined, preferably comprising a waveform based on reflective infrared signal and a waveform based on reflective red-light signal.

In an embodiment of the first variant, a constant component and a primary periodic component of each of said photoplethysmogram are determined.

In an embodiment of the first variant, defining a succession of frames includes defining intervals of said photoplethysmogram signal based on characteristics of said electrocardiogram signal and averaging values of said photoplethysmogram over a plurality of such intervals.

In an embodiment of the first variant, said constant components and said primary periodic components of said photoplethysmogram are determined from said average values.

In an embodiment of the first variant, said electrocardiogram includes an R wave signal each with a peak value in each of said heart beats and said intervals are determined with respect to the peak values of the R wave signals.

In a second variant of the pulse oximetry method, the photoplethysmography sensor comprises an optical lens surrounded by an adhesive layer and the optical lens is protruding, so as to maintain pressure great enough, to compress only the venous capillaries.

In a third variant of the pulse oximetry method, the photoplethysmography sensor is placed on a substrate intended to be adhered on the skin of the patient and protrudes from substrate by a thickness greater than 0.1 mm, preferably greater than 0.5 mm.

In a fourth variant of the pulse oximetry method, the photoplethysmography sensor is placed on the back of the patient, preferably near the nape of the neck, more preferably on a vertebra, ideally on T1 vertebra.

Features of all four variants may be combined, thereby increasing the mitigation of "venous shift" phenomenon.

Definitions

"SpO2" refers to peripheral oxygen saturation: an estimation of the oxygen saturation level (O2Sat) which is the percentage of hemoglobin binding sites in the bloodstream occupied by oxygen. Herein, SpO2 and O2Sat are equivalent.

"PPG" refers to a photoplethysmogram, i.e., the signal acquired by a photoplethysmography sensor as a function of time. The photoplethysmography sensor comprises light sources (usually light emitting diodes-LED-sources of determined colour in visible light or source of infrared light) and light detectors (usually photodiodes or other light sensitive sensors). Herein, PPG signal is an equivalent of PPG and PPG sensor refers to photoplethysmography sensor.

"ECG" or "EKG" refers to an electrocardiogram, i.e., the electrical signal linked to cardiac activity and acquired by electrodes. In particular, "lead 1 ECG" refers to the ECG signal acquired by electrodes and related to lateral direction of bipolar limb.

"ECG QRS" refers to the QRS complex, a combination of three graphical deflections seen on a normal electrocardiogram.

"PTT" refers to Pulse Transit Time, the time it takes for the heart pulse wave to travel throughout the body. In particular, PTT may be evaluated as the distance from the ECG QRS of a heartbeat and the peak of the PPG waveform associated to this heartbeat.

"Venous shift" refers to the skewing of PPG signal by light absorption in veins.

"Aggregated waveform" refers to a waveform which is a combination of a plurality of waveforms. The combination is preferably a simple sum, but may be also a weighted sum or a weighted average.

BRIEF DESCRIPTION OF THE DRAWINGS

FIGS. 2E and 2F show ECG and PPG signals (arbitrary units) versus time (seconds).

FIGS. 2G-I show PPG signal (red signal in bold solid line and infrared signal in dotted line-arbitrary unit) versus time (unit is time sampling period, here 1/64 second)

FIG. 5A shows device placed on a patient in supine position.

FIG. 5B shows device placed on a patient lying on his/her side: a pectoral force P is applied and device bends at the pleat, thereby creating a moment M on the part of device comprising the PPG sensor 511 and finally increasing pressure P' applied to the patient below PPG sensor.

In FIG. 5C, venous (V) and arteria (A) are slightly compressed as PPG sensor 511 is just in contact with the patient's skin. In FIG. 5D, a compressible adhesive foam 513 is used allowing the PPG sensor 511 to protrude from device, thereby increasing pressure applied on patient's body and leading to compression of venous capillaries (V) so that they contribute less to PPG signal whereas blood pressure keeps arteria (A) well open so that they contribute normally to PPG signal.

FIGS. 9A and 9B are measurement for a patient with light skin (Fitzpatrick score of 2). FIGS. 9C and 9D are measurement for a patient with dark skin (Fitzpatrick score greater than 6).

DETAILED DESCRIPTION

Figure 1A:
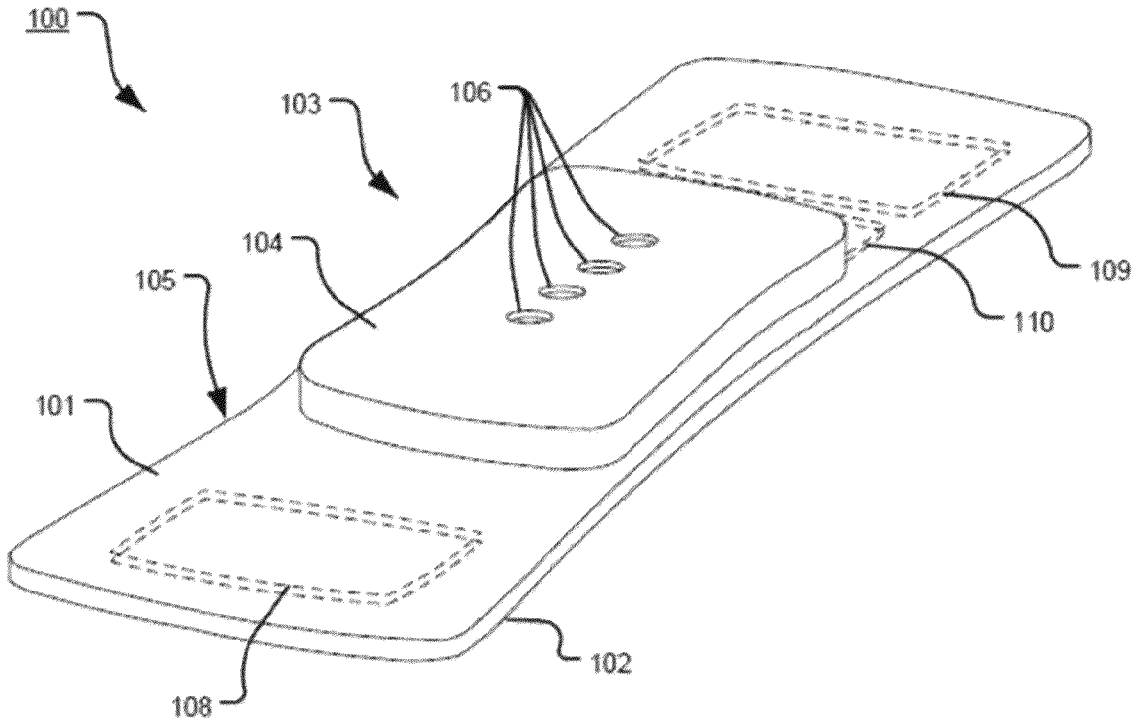
FIGS. 1A-1G illustrate several alternatives of a device suitable to implement pulse oximetry method disclosed herein.

While the inventions hereof are amenable to various modifications and alternative forms, specifics hereof have been shown herein by way of non-limitative examples in the drawings and the following description. It should be understood, however, that the intention is not to limit the inventions to the particular embodiments described. The intention is to cover all modifications, equivalents, and alternatives falling within the spirit and scope of the inventions whether described here or otherwise being sufficiently appreciable as included herewithin even if beyond the literal words or figures hereof.

In general, included here are on-body, multi-function, biometric sensors. The devices monitor bodily functions such as one or more or all of ECG, PPG, temperature, respiration, and activity among other possible options. Such devices may in many cases be configured for operational attachment to, on, adjacent to, or nearby a subject's sternum or on a subject's chest or a subject's back with an adhesive, often a disposable adhesive. Such devices may typically be in many instances, but not limited hereto, small and thin relative to a user (e.g., on the order of approx. +\—~1.5"× 3"×¼" or approximately 30 mm×100 mm×6.3 mm; practical sizing not limited hereby, but may be dependent inter alia on body size and practical component availability among other features) and may typically be configured to be wearable by a wide range of subjects from infant to adult through to the morbidly obese.

In one aspect, a system hereof may include a device for monitoring physiological parameters such as one or more or all of electrocardiogram (aka ECG or EKG), photoplethysmogram (aka PPG), pulse oximetry, temperature, respiration, and/or patient acceleration or movement signals and/or audio or sound signals as for example heartbeat or breathing sounds.

In some implementations, devices hereof may be for comprehensive long-term cardiac monitoring, inter alia. Features of such may but not necessarily include any one or more of a Lead 1 ECG, PPG, pulse oximeter, accelerometer, temperature sensor and/or a button or other indicator for manual patient event marking. Such a device may be adapted to communicate in real-time or near real-time to display vital signs as or very near in time as they are occurring. In some other implementations, such a device may rather store up to, for example, about two weeks of continuous data (though more or less will also be feasible in alternative implementations), which may in some implementations be downloaded to a clinic or other computer in a short time period, as for one example, in only about 90 seconds (though more or less time will be viable in alternative implementations) via computer connection, whether wireless or wired as in one example by USB or other acceptable data connection. In real-time or near real-time implementations, data communication may be via hard-wire connection, or may be by Bluetooth or other wireless data communication, and may be direct to a display monitor or computer for display, or may occur over a network, or even via cellular communication and may include data communication to one or more remote servers, e.g., the 'cloud' for further communication to a display or remote computer. A companion software data analysis package may be adapted to provide automated event capture and/or allow immediate or delayed, local data interpretation.

Intermittent cardiac anomalies are often difficult for physicians to detect and/or diagnose, as they would typically have to occur during a physical examination of the patient. A device hereof may address this problem with what in some implementations may be a continuous or substantially continuous monitoring of one or a number of vital signs.

Figure 8A:
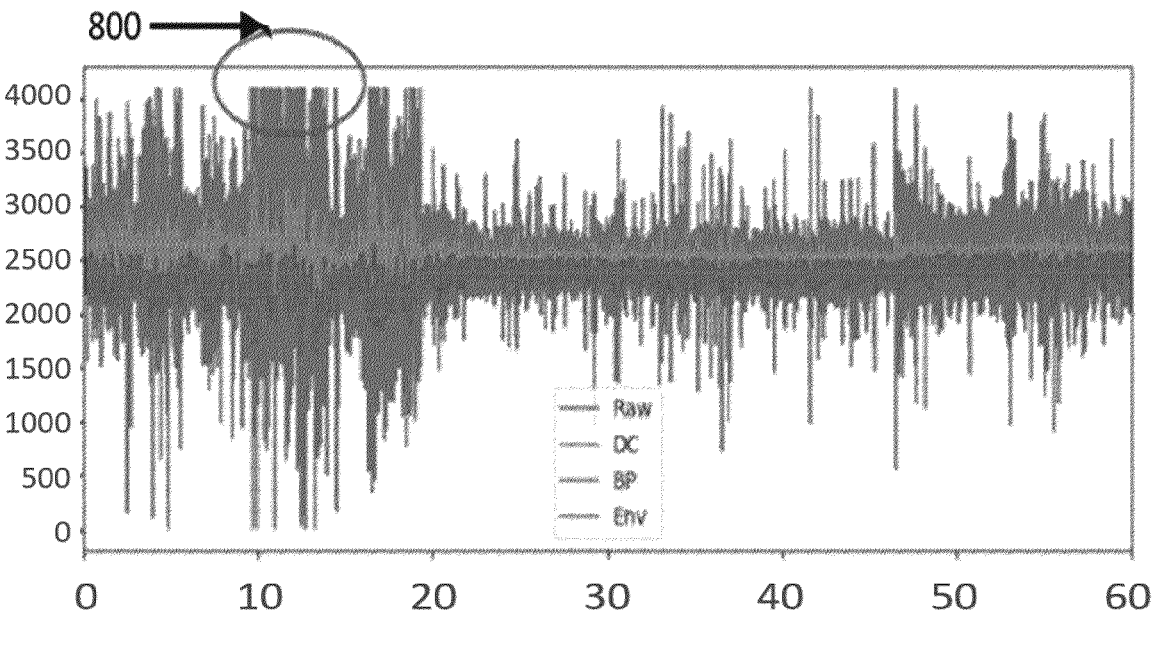
FIG. 8A shows a PPG signal (arbitrary unit) versus time (seconds). In highlighted area 800, saturation of signal occurs.
Figure 8B:
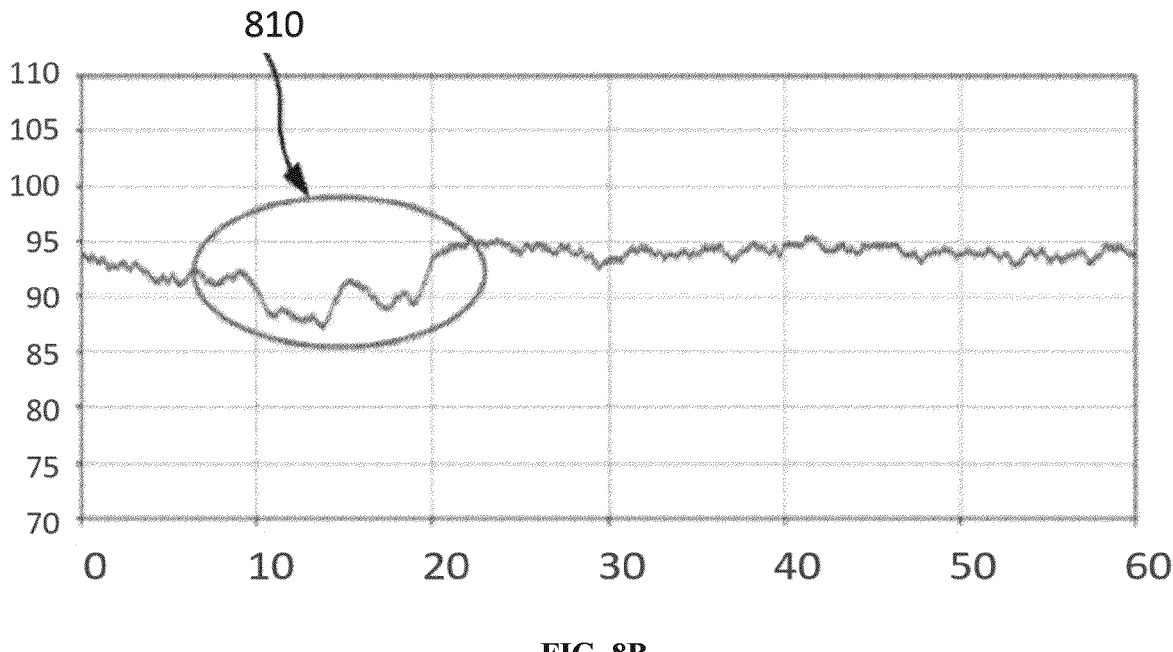
FIG. 8B shows the corresponding SpO2(%) versus time (seconds). In highlighted area 810, a decrease of SpO2 appears, actually an artifact linked to saturation of PPG signal.

In some alternative non-limiting implementations, the sensor systems may include expanded dynamic range of the signal acquisition circuitry. The signal of interest in the PPG signal is a small pulsatile wave. This pulsatile wave must be highly amplified to obtain the needed resolution for the calculation and derivation of the oxygen saturation (SpO2) levels. In certain instances, the amplification in or with the presence of motion artifacts may cause the signal to saturate the amplifier and may result in signal loss. For example, while using a 12 bit A/D (analog-to-digital) converter the range of measurement of the raw PPG signal was about 4096 levels. The results of using this combination of amplifier and converter is shown in graphical form in FIG. 8A. The over-saturation and signal misrepresentation is shown by the circled area 800. This circled area shows where the PPG signal is saturating, or sometimes referred to as railing. In FIG. 8B, the circled area 810, shows how the derived SpO2 levels may be misrepresented and/or distorted as a result of the loss of signal from the PPG due to the saturating, or railing described in FIG. 8A. Increasing the A/D converter from 12 bits to 24 bits represents approximately a 60 dB gain in the dynamic range. The use of a 24 bit A/D converter may help eliminate the possibility of saturating the amplifier and the resulting distorted derived SpO2 levels as shown in FIGS. 8A and 8B.

In some alternative non-limiting implementations, the sensor systems may have dynamic automatic gain control for optimizing and maximizing signal acquisition depending on the physiology of the patient. A fixed gain amplifier may not be appropriate for all physiologies. For example, a very dark-skinned patient will require a relatively high level of gain; however, a light-skinned person may require a much lower level of gain. A fixed gain amplifier may limit the ability to maximize and optimize the pulsatile signal for all physiologies. Therefore, devices hereof may have many different levels of gain control, in some instances as many as 2, 3, 4, 5, 6, 7, 8, 9, or more different levels of gain control. These different levels of gain control may thus allow for automatic setting of the appropriate level of gain for different physiologies encountered.

In some implementations the device hereof may allow for 512 levels of DC Offset. With this control, the signal will always be placed in the middle of the amplifier range, allowing for maximum amplification and limited distortion. DC Offset allows for the signal to be set correctly in the middle of the amplifier input range. If the DC Offset is not incorporated in to the device hereof, very dark skin may cause the DC offset to be near the bottom of the range of the amplifier, limiting the ability to amplify the signal without significant distortion.

In some implementations the device hereof may have 256 levels of LED light control that may allow more efficient control for each physiology to increase efficiency of the device and extend the device wear time. As with amplifier gain, different physiologies require different amount LED light intensity. Since LED power is one of the largest consumers of battery power in the system, inefficient control, management, or usage of the LEDs may result in inefficient battery usage and thus decreased longevity or wear time.

Figure 9A:
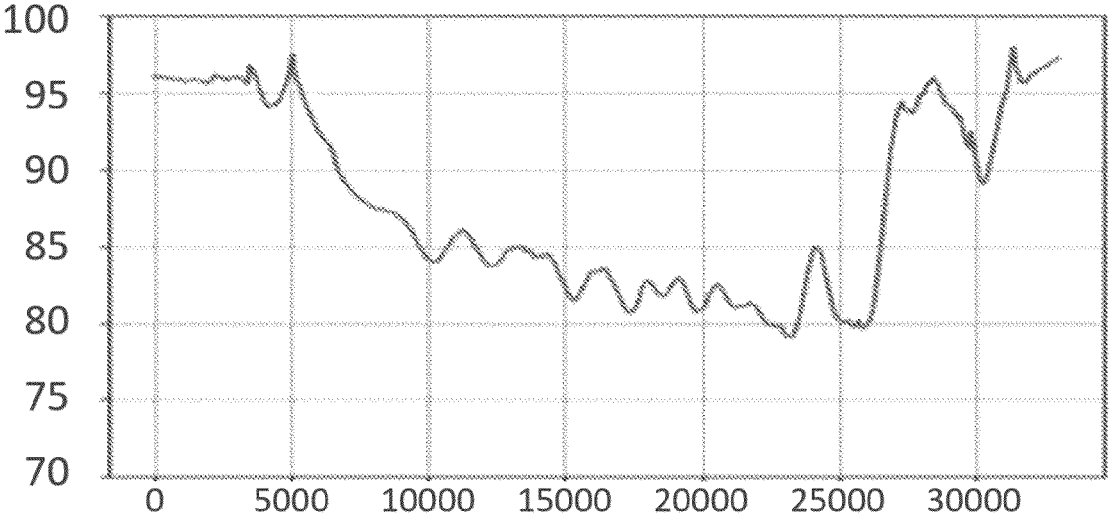
FIGS. 9A-D compare results of a SpO2 measurement (%) versus time (seconds) with the device disclosed herein (9A and 9C) compared to a commercial finger oximeter (9B and 9D).
Figure 9B:
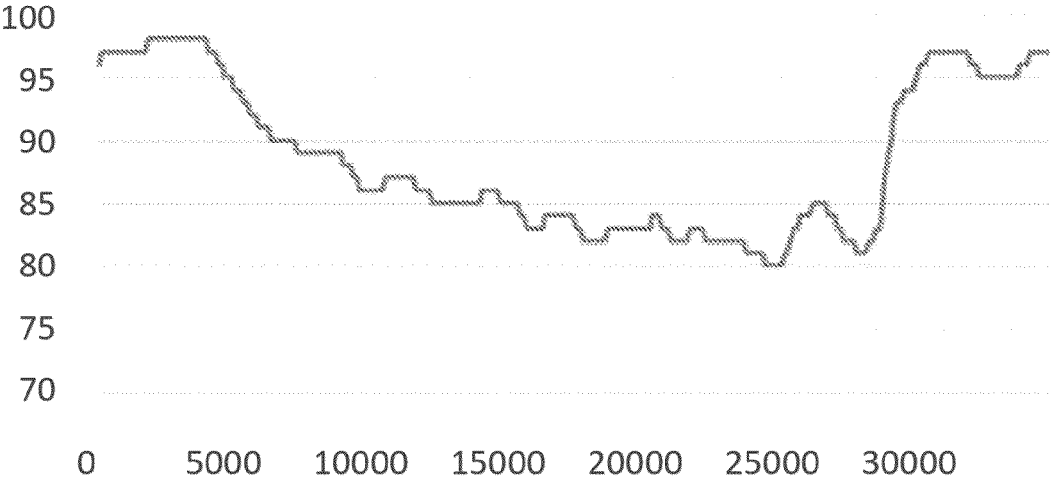
Figure 9C:
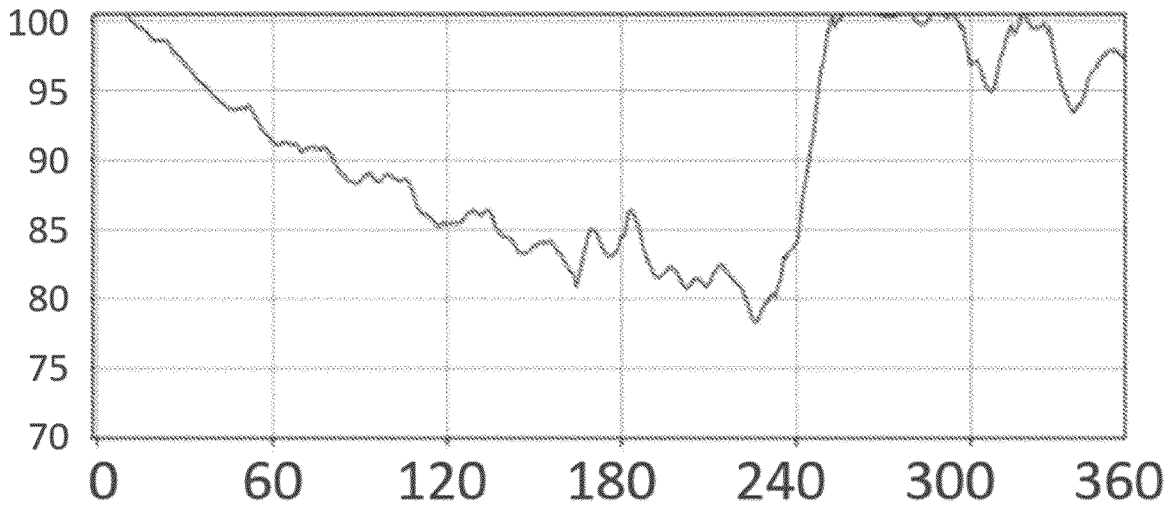
Figure 9D:
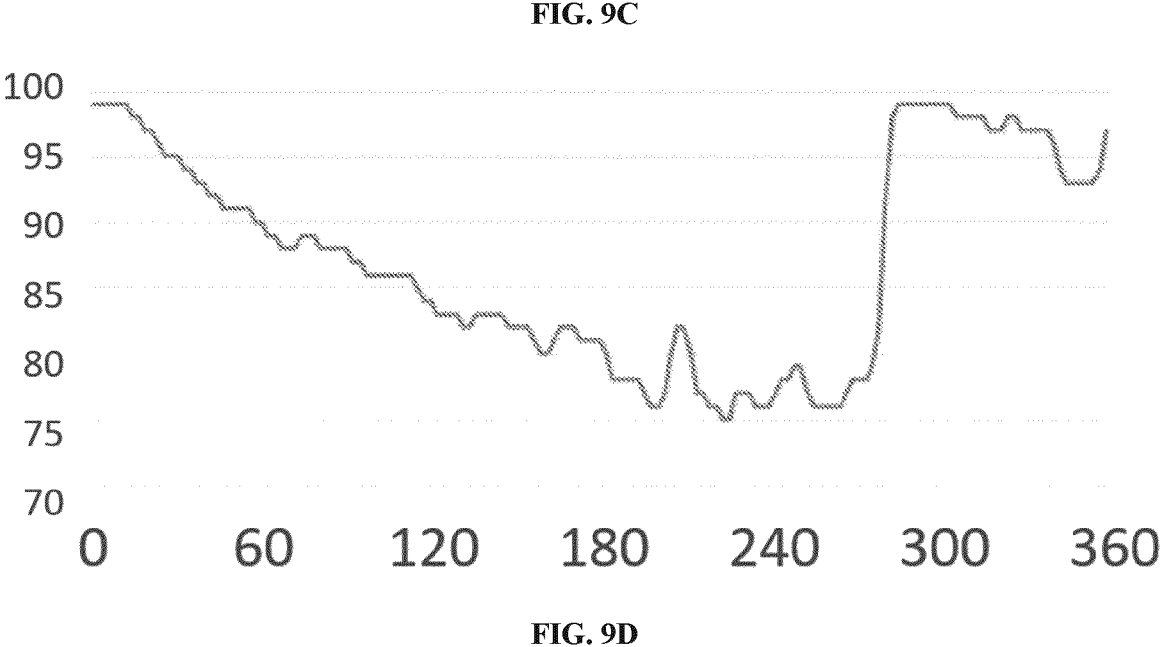

FIGS. 9A and 9C show the results of Sp2 measurements by the device hereof. FIGS. 9B and 9D provide the results of SpO2 measurements of a commercial finger oximeter. Note that in FIGS. 9A and 9B, the tests were performed simultaneously on an individual with light skin, with a Fitzpatrick score of 2. In FIG. 9A the device hereof was placed on the chest of the individual and in FIG. 9B the finger pulse oximeter was placed on the finger of the individual. Note that in FIGS. 9C and 9D, the tests were simultaneously performed on individuals with very dark skin, or a Fitzpatrick score greater than 6. In FIG. 9C the device hereof was placed on the chest of the individual and in FIG. 9D the finger pulse oximeter was placed on the finger of the individual. In both tests, that is, whether on a very light skinned person or a very dark-skinned person, the device hereof was capable of providing results very similar to those of a commercially produced finger pulse oximeter, which demonstrates that the device hereof may provide accurate information regarding SpO2 levels over time.

In some implementations the wearable device hereof may be approximately 80 mm (~3.149 inches) in length. In some aspects as shorter length may increase wear time of the device by decreasing the device's loss of adhesion and electrode lifting or detachment which may occur if the device is too large for a particular physiological topography. Further in some implementations the device may incorporate a circuit board design that is more flexible which may enable a greater integrity of adhesion to the subject.

In some alternative implementations of the device hereof, the device may utilize only two (2) electrodes for obtaining the data needed for the ECG measurements and calculations. In one aspect the use of two electrodes may increase the reliability of the device because there may be a lower or lesser change of electrode lifting and subsequent signal loss. Additionally, in some implementations one electrode may be integral to the main body of the strip, while the second (or a third) electrode is tethered, which may de-couple the mechanical movement of the two electrodes and thus greatly reduce or decrease motion noise from the signals obtained from each electrode. The tethered electrode may allow different relative positioning of the electrodes as the tethered electrode is attached via a flexible electrode extender. One benefit of a being able to change the relative positioning of the electrode may be that different ECG morphologies may be required for particular studies, and thus being able to change the placement of the electrode may allow the device to be used in studies requiring devices that can measure different ECG morphologies. Moreover, in some implementations an analog front-end (AFE or analog front-end controller (AFEC)) set of conditioning circuitry that utilizes high sensitivity amplifiers and filters along with the automatic gain control (described elsewhere herein) may allow for greater reliability and ECG resolution for all ages and physiologies.

Figure 1B:
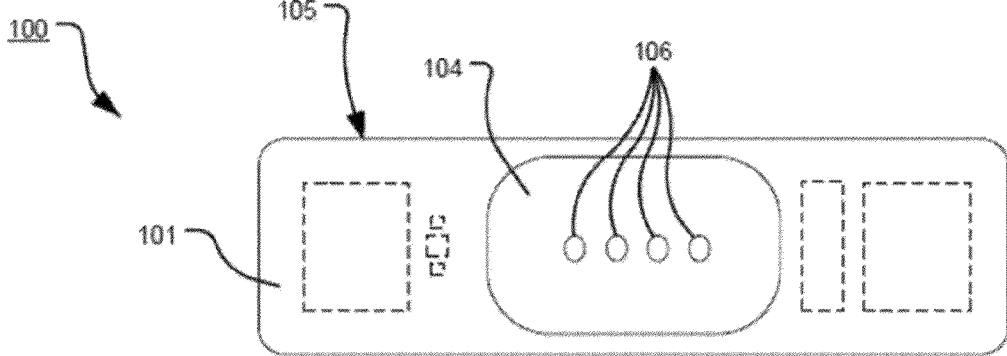

FIG. 1, which is defined by and includes any and/or all of sub-part FIGS. 1A-1G, shows a device 100 (or 500 or 500a) that has a component side or top side 101 (or 501), patient side or circuit side 102 (or 502), and one or more inner electrical layer(s), generally identified by the reference 103 (or 503) and an elongated strip layer 105 (or 505). The strip layer 105 may have electronics thereon and/or therewithin. FIG. 1A shows isometrically these in what may in some non-limitative implementations be considered a substantially transparent device together with some other elements that may be used herewith. FIG. 1B is more specifically directed to a top side 101 plan view and FIG. 1C to an underside, patient side 102 plan view and FIG. 1D a first elevational, side view.

Figure 1C:
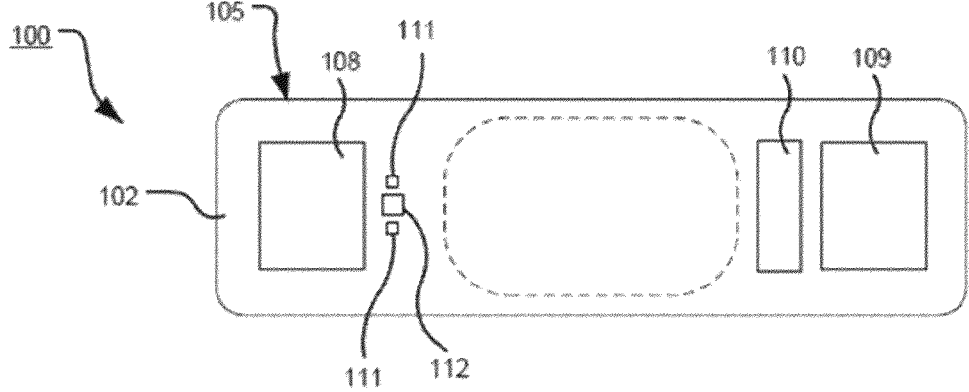
Figure 1D:
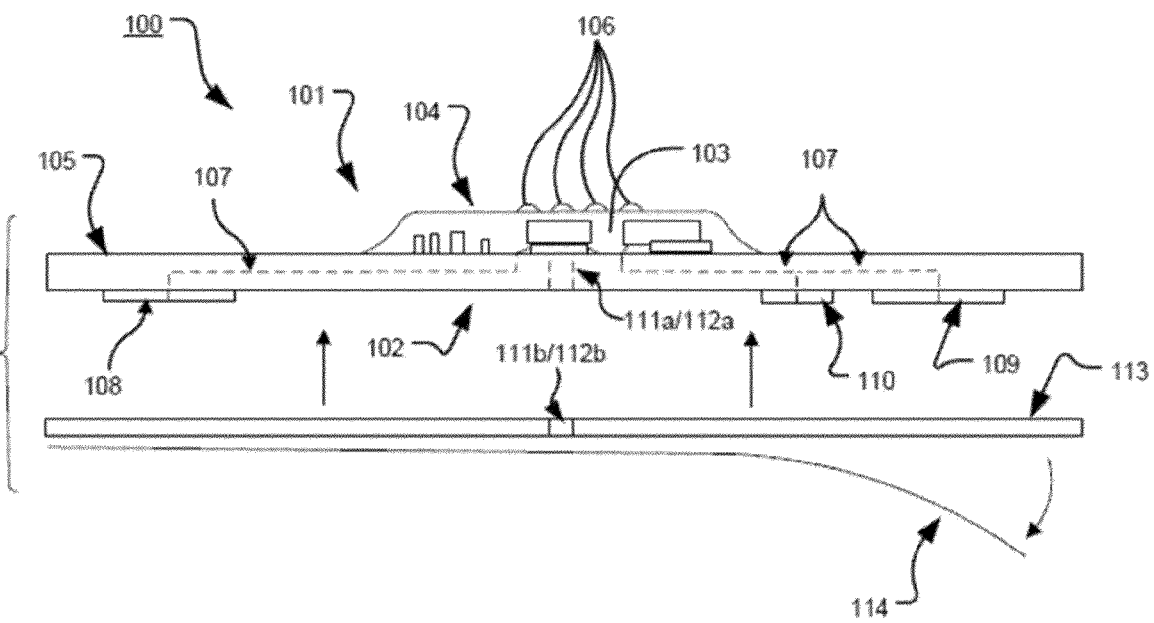

Many of the optional electronics hereof may be disposed in the electronics layer or layers 103, and as generally indicated here, the electronics may be encapsulated in a material 104 (or 121a) (see FIGS. 1A, 1B, 1D, and IF for some examples), medical grade silicone, plastic or the like, or potting material, to fix them in operative position on or in or otherwise functionally disposed relative to the elongated strip layer 105. The potting or other material may in many implementations also or alternatively provide a waterproof or watertight or water-resistant coverage of the electronics to keep them operative even in water or sweat usage environments. One or more access points, junctions or other functional units 106 may be provided on and/or through any side of the encapsulation material 104 for exterior access and/or communication with the electronics disposed therewithin, or thereunder. FIGS. 1A, 1B and 1D show four such accesses 106 on the top side. These may include high Z data communication ports and/or charging contacts, inter alia. This upper or component side 101 of device 100 may be coated in a silicone compound for protection and/or waterproofing, with only, in some examples, a HS USB connector exposed via, e.g., one or more ports 106, for data communication or transfer and/or for charging.

The elongated strip layer 105 (or 505) may be or may include a circuit or circuit portions such as electrical leads or other inner layer conductors, e.g., leads 107 shown in FIG. 1D, for communication between the electronics 103 (or 503) and the electrically conductive pads or contacts 108, 109 and 110 described further below (108 and 109 being in some examples, AgCl (printed or otherwise), high impedance/high Z silver or copper/silver electrodes for electrocardiograph, ECG, and 110 at times being a reference electrode). In many implementations, the strip layer 105 (or 505) may be or may include flex circuitry understood to provide acceptable deformation, twisting, bending and the like, and yet retain robust electrical circuitry connections thereon and/or therewithin. Note, though the electronics 103 and electrodes 108, 109, 110 are shown attached to layer 105; on top for electronics 103, and to the bottom or patient side for electrodes 108, 109, 110; it may be that such elements may be formed in or otherwise disposed within the layer 105, or at least be relatively indistinguishably disposed in relative operational positions in one or more layers with or on adjacent layer 105 in practice. Similarly, some of what may be myriad possible leads or traces 107 are shown embedded (by dashed line representation in FIG. 1D); however, these may be on the top or bottom side, though more likely top side to insulate from other skin side electrical communications. If initially top side (or bottom), the traces may be subsequently covered with an insulative encapsulant or like protective cover (not separately shown), and/or in many implementations, a flexible material to maintain a flexible alternative for the entire, or majority of layer 105.

Figure 5A:
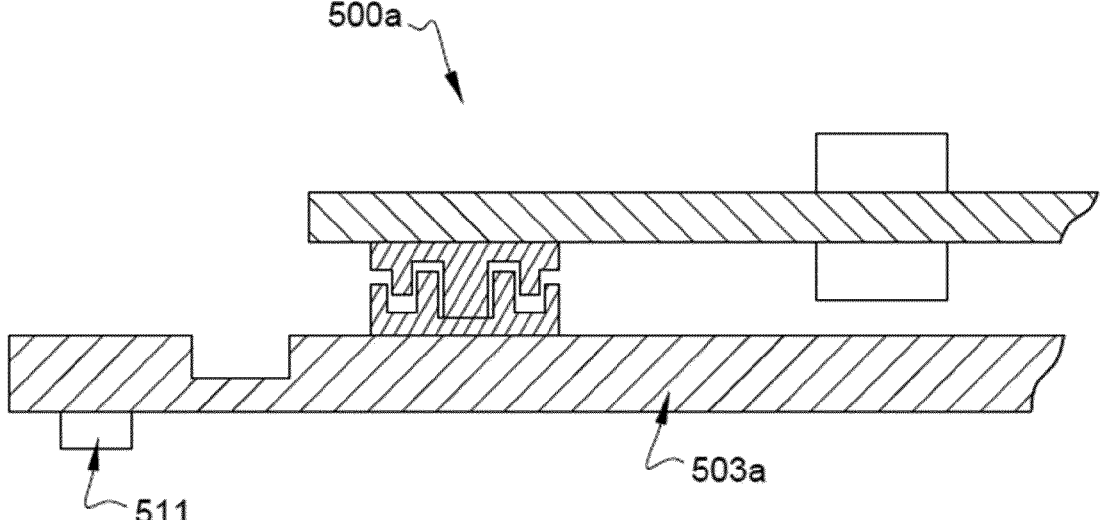
FIGS. 5A-B illustrate an embodiment of device allowing to mitigate venous shift by compression of venous capillaries.

In the implementations of FIGS. 1A-1D (among others also shown and described below), all the circuitry is shown attached relatively directly to the flexible circuit board 105, though still viable options, but may perhaps less preferred with current flexible substrates. However, in some alternatives, in order to make the subject-facing Flexible Card Board relatively more flexible than the board 105 of FIGS. 1A-1D, many if not all of the large Integrated Components and other components can be relocated to another, relatively rigid, Printed Circuit Board (aka PCB) that can be nevertheless operably connected to a flexible circuit board. These are shown in FIGS. 1E and 5A in the devices 500 and 500a.

Figure 1E:
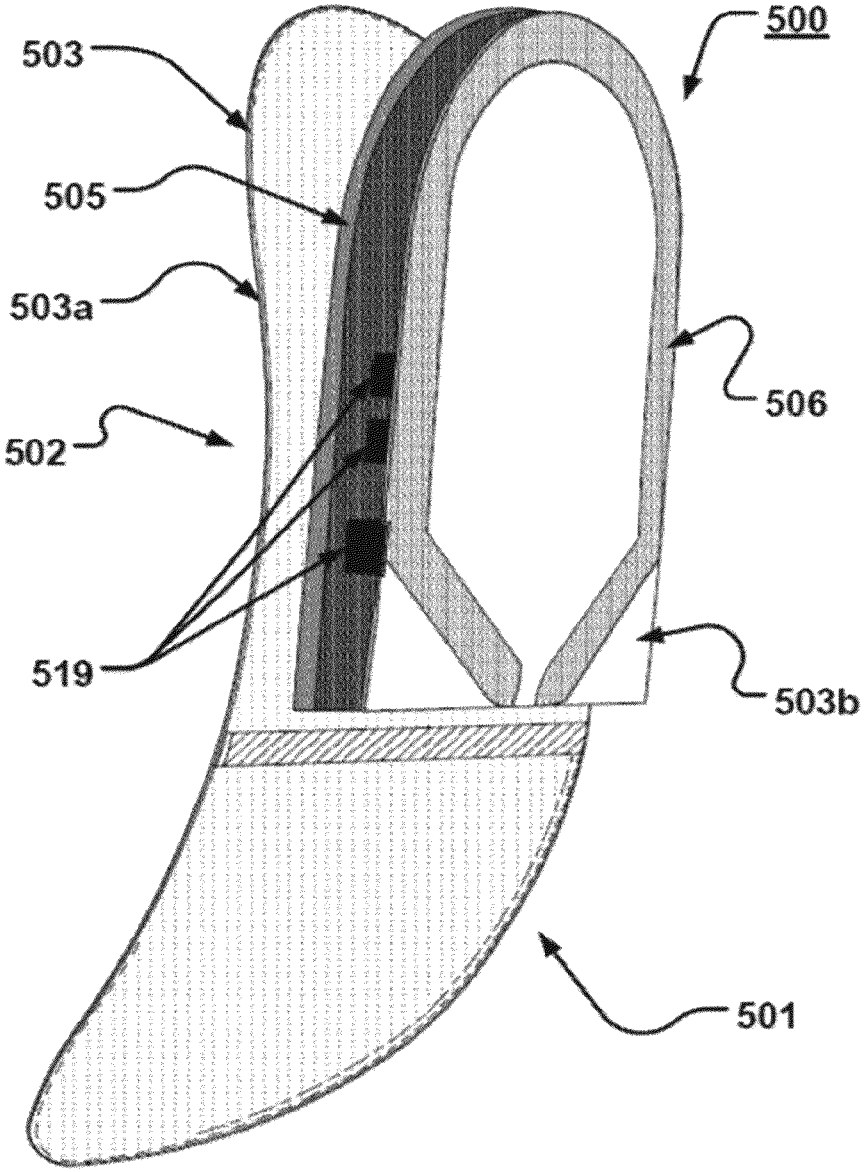
Figure 1F:
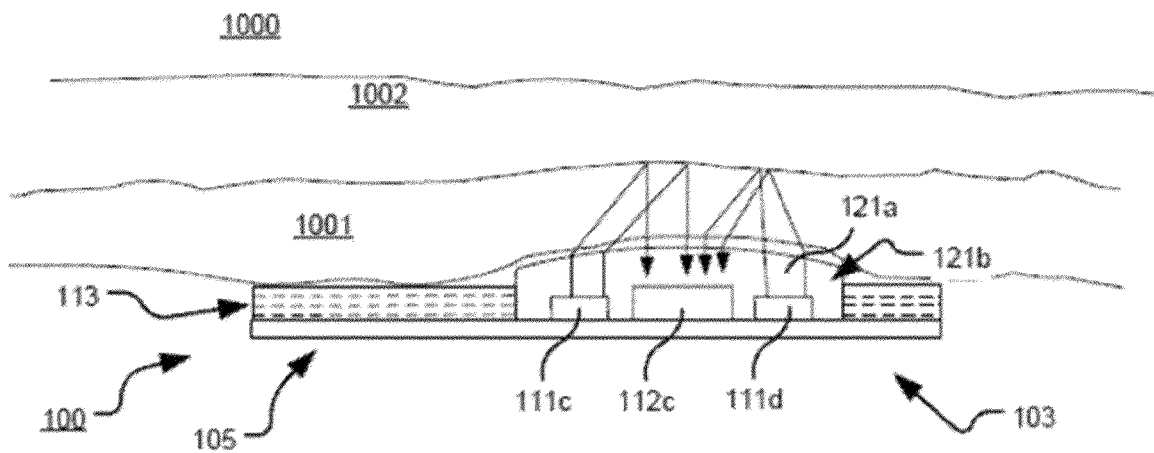
Figure 1G:
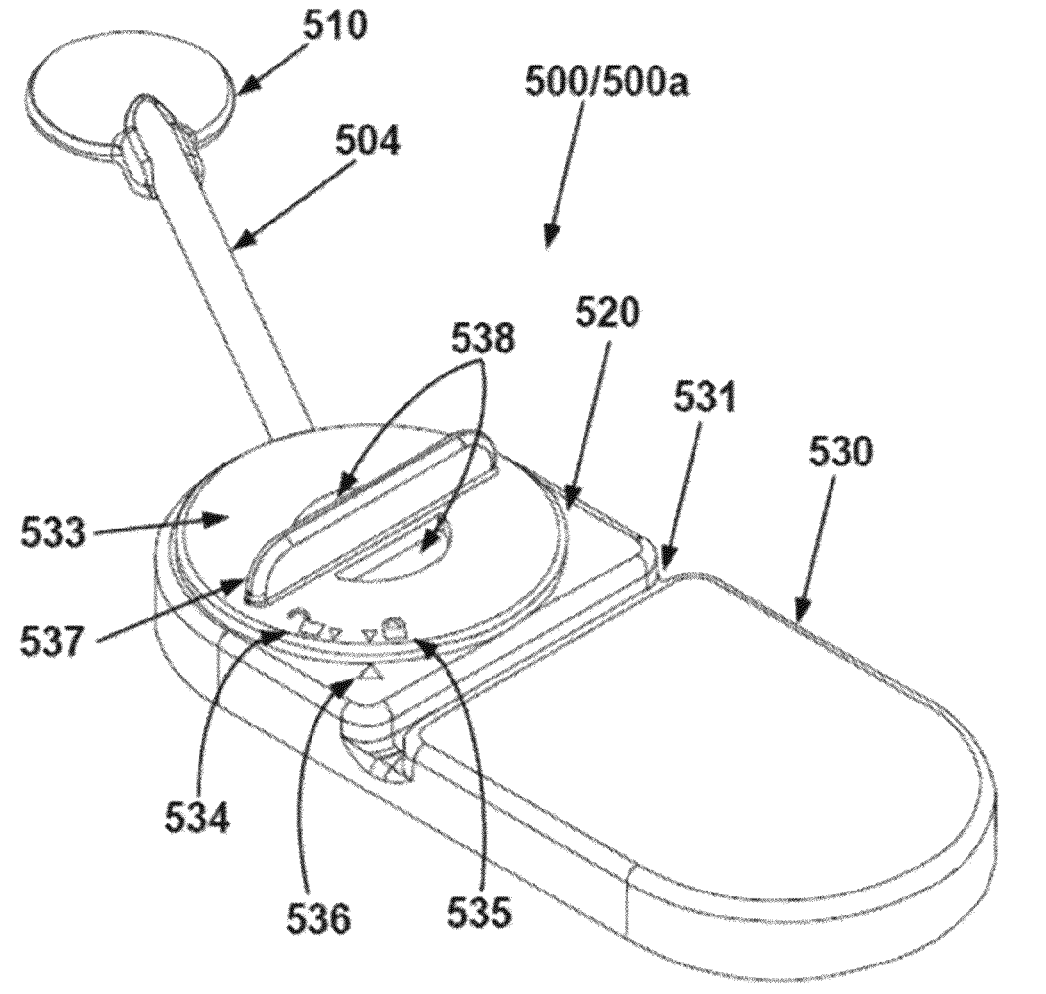
Figure 4A:
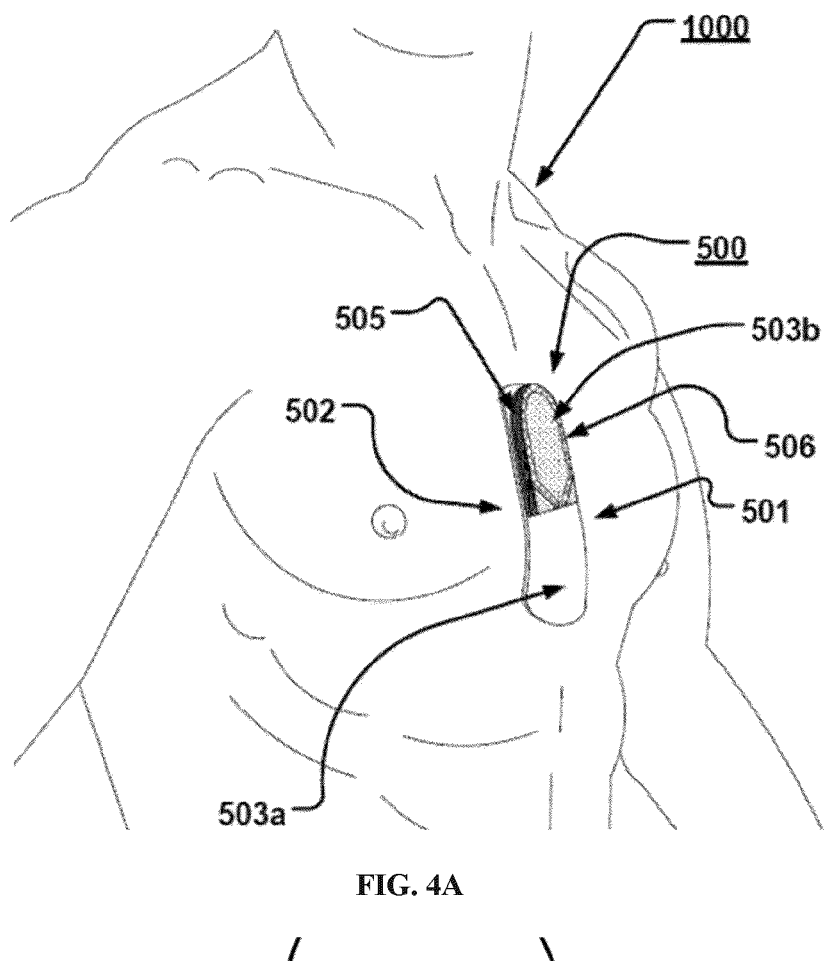
FIG. 4A shows application of a device on the sternum of a patient.
Figure 4B:
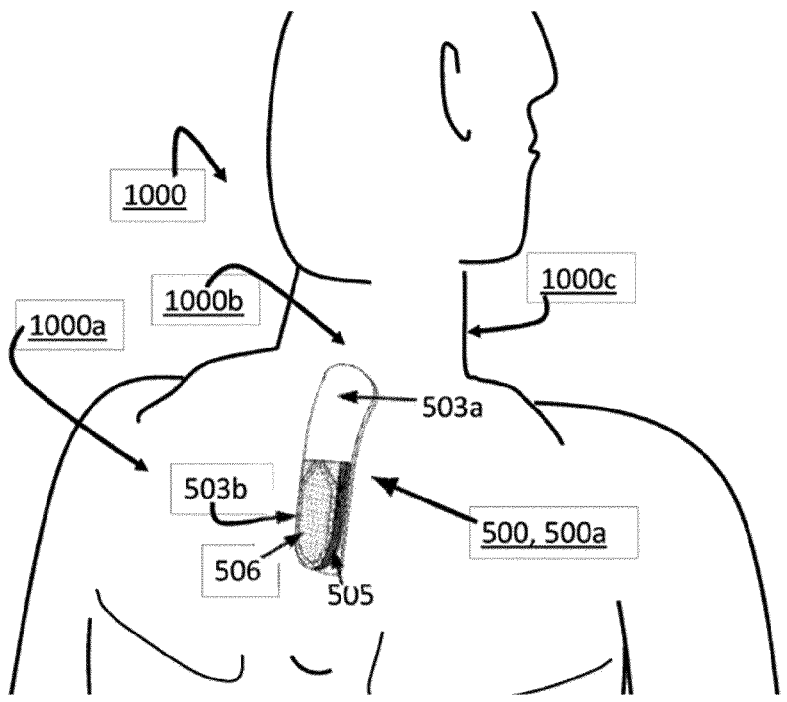
FIG. 4B shows application of a device on the back of a patient.

In more particularity, sub-part FIGS. 1E and 1G show a device 500 or an alternative device 500a that each have a component side or top side 501, patient side or circuit side 502, and one or more generally electrical layer(s), generally identified by the reference 503, generally. Also here included is an elongated strip layer or circuit layer 505 disposed therewithin. The circuit layer 505 may have electronics thereon and/or therewithin, for instance the ECG electrodes, the PPG device/sensor, a temperature sensor and a microphone, e.g., a piezo microphone. FIGS. 1E, 4A and 4B show isometrically these in what may in some non-limitative implementations be as shown a substantially transparent or translucent device together with some other elements that may be used herewith. FIGS. 1E, 4A and 4B show two or more layers, generally one on top of the next, here including a first layer 503*a* which is a flexible or flex circuit layer shown noticeably flexed, here shown arched as it might be in use on a subject user (a user or wearer 1000 is identified generally in FIGS. 4A and 4B. The second or middle circuit layer 505 is here a relatively rigid material board not intended to arc or arch or otherwise flex to more readily maintain the electrical connections and/or circuit components connected thereon, thereto and/or therewithin. An optional third layer 503*b*, also here a flexible layer is also shown, here above the circuit layer 505; the third layer 503*b* here having data communication capability, via one or more data communication devices 506, here via an antenna 506.

A description of the antenna 506 is that it may preferably be designed to fit, e.g., may be custom fit, within the envelope of the device 500/500*a*. It may be resonant at 2.4 GHz with a Minimum Standing Wave Ratio and Maximum Forward Power. In order to achieve this, active element length, width, and dielectric thickness may be optimized in-situ, on the human body, with the circuit boards, silicone cover, and adhesives in place. A novel feature may normally be a dipole antenna is normally constructed with two elements of equal length at the resonant frequency (one passive, one active). The herein shown and described implementation of a dipole may use an active element at the resonant frequency, but the human body as the passive element.

FIG. 1G provides a three-dimensional top view of a device 500 or 500*a* or the like, including optional third electrode 510 (tethered electrode), electrode extender 504, silicone cover 530, pleat 531, battery cage 520, and removable battery cage cover 533. The removable battery cage cover 533 may be a turnable friction-fit type (or alternatively a bayonet style) of cap that allows the cap to be secured in place relative to the battery cage 520. In some implementations, the removable battery cage cover 533 may have an unlock indicator 534 and lock indicator 535, that align with a point of reference marking 536 to help a user determine whether the removable battery cage cover 533 is secured in place relative to the battery cage and the device more generally. Further, in some implementations the battery cage cover 533 may further have a handle 537 that protrudes from the surface of the battery cage cover that may assist the user in turning (screwing or unscrewing) and securing the battery cage cover. Alternatively, the battery cage cover 533 may also have one or more indentations 538 to assist the user in turning (screwing or unscrewing) the battery cage cover. In some instances, the battery cage cover may have a sealing material of silicon, rubber, or other suitable material (not shown in diagrams) around the circumference of the bottom-side of the cap to provide for waterproofing of the battery compartment from the exterior conditions.

Returning to description of other components, on the patient side 102, as in FIG. 1C, the ECG electrodes 108, 109 and 110 may be left exposed for substantially direct patient skin contact (though likely with at least a conductive gel applied therebetween); and/or, in many implementations, the patient side electrodes 108, 109 and/or 110 may be covered by a conductive adhesive material as will be described below. The electrodes may be plated with or may be a robust high conductive material, as for example, silver/silver chloride for biocompatibility and high signal quality, and in some implementations may be highly robust and, for one non-limiting example, be adapted to withstand over about one thousand (1000) alcohol cleaning cycles between patients. In some instances, these silver/silver chloride electrodes may be printed directly on the flexible circuit board or flexible printed circuit, and yet in other instances the silver/silver chloride electrodes may be attached or fastened to the flexible circuit board or flexible printed circuit as a discrete and separate step in the fabrication process. Windows or other communication channels or openings 111, 112 (FIG. 1C) may be provided for a pulse oximeter, for example, for LEDs and a sensor. Such openings 111, 112 (e.g., FIG. 1C) would typically be disposed for optimum light communication to and from the patient skin. An alternative disposition of one or more light conduits 111*a/*112*a* (and 111*b/*112*b*) is shown in a non-limiting example in FIG. 1D more nearly disposed and/or connected to the electronics 103. A variety of alternative placements may be usable herein/herewith, some of which further described below.

In some implementations, sampling of the ambient light (with the LEDs off) may be provided, and then subtracting this from each of the pulse-oximetry signals in order to cancel out the noise caused by sunlight or other ambient light sources.

The combination of LEDs and photodiodes/sensors might also be referred to in some implementations as a High-Efficiency Integrated Sensor. This arrangement may be implemented in determination of SpO2 (peripheral capillary oxygen saturation).

In FIG. 1F an implementation of a silicone covering or encapsulant 121*a* for the LEDs and sensor 111*c/*111*d/*112*c*, may include a convex lens at or adjacent the covering external surface 121*b*. In many implementations, the external surface and lens are one and the same and/or the lens may be defined by the surface 121*b* of the encapsulant material 121*a*. What this provides is a structure and method for interfacing pulse oximetry LED emitters 111*c/*111*d* and one or more photodiode sensors 112*c* with the skin surface, whether chest or forehead (e.g., infant or neonate) or back or otherwise mounted on the patient or user body. In an alternative option, the PPG is attached to the flexible substrate 503*a* and may protrude slightly from the adhesive layer 113 and make contact with the skin 1001 of the wearer 1000. Note that in this implementation the device 100 may be operably connected to the PPG unit including LEDs 111*c* (Red LED) and 111*d* (Infrared LED), and optionally Green LED (not shown). The LEDs project light into the skin of the patient where it penetrates the tissue and then is reflected or scattered back towards the photodiode or photosensor. In FIG. 1F, the bone 1002 of the patient is shown in the diagram as well. The PPG sensor shown in FIG. 1F may be about 5 mm$^2$ and the diameter of the exterior circle encompassing the sensors and LEDs might be a corresponding about 8 mm. In some implementations, it may be that about 3.2 mm red may be set for a preferred distance from the center of the red LED light sources to the center of the corresponding sensor, and may be a preferred distance of about 3.7 mm set from the center of the Infrared LED light sources and green LED light sources to the corresponding sensor.

More particularly, as otherwise described herein, a system and/or device 100 hereof may utilize one or multiple LED emitters 111*c/*111*d* (and optionally more) of selected wavelengths and one or multiple photodiode sensors. However, in order to maximize coupling of the LED/sensor combination to the skin 1001 of a wearer 1000, an encapsulant and/or lens 121*a/*121*b* comprised of optically clear, medical grade silicone may be molded onto or molded such that it may be later attached in covering relationship on the LED/sensor combination 111c/111d/112c. In many implementations, as for example in FIG. 1F, the lens 121b may be partially spherical or perhaps hemispherical in nature. Curvature of other shapes may be useful as well. Curvature may reduce loss of skin contact when the device 100 may be moved, whether by wearer motion or otherwise. I.e., motion of the wearer 1000 or the device 100 relative to the wearer 1000 in FIG. 1F can result in a quasi-rolling contact of the lens on and in relation to the skin 1001. Better maintained skin contact means better data acquisition without interruption and/or with reduced noise.

As a further note, for a curved lens 121b option as from FIG. 1F, the radius of the lens may be designed to maximize light propagation from light sources 111c/111d to light sensor 112c after transmission through patient's skin 1001 and reflection on patient's bones 1002. The height of the lens may be designed to allow it to protrude above composite adhesive 113 of the device 100 and into the skin, but not deep enough to disturb the capillary bed which would also result in bad data. Moreover, the radius of curvature and the angles of LED lightwave emission are not necessarily highly controlled and need not be because the LEDs used to penetrate the skin, e.g., the red and infra-red and/or green LEDs; provide a very wide array of angles of emission, and thus a large number of reflected array of lightwaves will be focused back to the sensor by a large variety of curved surfaces. I.e., the curved surface is helpful for maintaining contact through movement (accidental or on purpose), and is less important to the angles of transmission through the skin and reflection back to the sensor. In other words, many different radii of curvature will be effective with very little difference in data/wave transmission and reflection; the wide-angle emission of LED takes care of what might be a variety of radii. Rather, the curvature may have more limitation in the maintenance of contact due to movement of the device 100—e.g., flatter curvatures will not roll readily, and very small radii of curvature will not transmit or receive as much data.

In some implementations, a radius of curvature found useful has been between about 20 and 40 (both 20.34 mm and 39.94 mm radii of curvature have been found useful) for a device having LEDs and sensors in a compartment of about 12.6 mm by 6.6 mm. It may be noted further that LEDs may be on one side or another or on two opposing sides or perhaps at four or more substantially equi-distant points around a sensor and may provide desirable results.

Note further, pulse oximetry hereof may be with multiple light sources and/or sensors. Typical pulse oximetry circuitry uses one light source (LED) per wavelength (typically red, infrared, and sometimes others including green or long-time averages of red/infrared for further examples as described below). However, devices and/or methods hereof may make use of multiple light sources for each wavelength. This may allow for interrogation of a wider area of capillary bed in/on the patient/wearer in order to reduce the effects of a local motion artifact. Similarly, multiple sensors may be used for the same or similar purpose or advantage.

Thus, measurement of arterial blood oxygen content can be made using optical signals (sometimes also referred to as heart beat optical signals), typically from red and infrared pulsed sources, which exhibit different optical absorptions dependent on oxy-hemoglobin presence or absence. In sum, a transmissive system is used with light sources and optical detectors.

Herein, reflective systems are typical, and these often have some advantages being less intrusive, and perhaps being more portable. As described herein, such reflective systems typically employ a red and an infra-red source and a photo-diode sensor or detector, or multiple arrangements of these components. Also as described, one implementation/method employs one or more central large area photo-diodes/sensors/detectors, with one or more LED sources, often one or more of each of a red, and an infra-red LED sources adjacent to the photo-diode or in an array around it. Also as described, an alternative arrangement uses a central LED set of one or more light sources, with one or more of each wavelength type (red, infrared, optionally Green, etc.), and multiple large area photo-diodes or light sensors surrounding the central LEDs. Such an arrangement might use two or three or four such detectors around the LEDs to collect more light scattering from the LEDs through the skin and other tissues.

Returning to the adhesive alternatives, FIG. 1D provides a first example of an adhesive 113 that may be used herewith. The adhesive layer 113 is here a double-sided adhesive for application to the bottom side 102 of the device 100 or alternatively the device 500, and a second side, perhaps with a different type of adhesive for adhering to the skin of the human patient (not shown). Different types of materials for adhesion might be used in that the material of choice to which the adhesive layer is to be attached are different; typically, circuit or circuit board material for connection to the device 100, and patient skin (not separately shown) on the patient side. A protective backing 114 may be employed on the patient side until application to the patient is desired. Note, in many applications, the adhesive 113 is anisotropic in that it may preferably be only conductive in a single or substantially a single direction, e.g., the axis perpendicular to the surface of adhesive contact. Thus, good electrically conductive contact for signal communication can be had through such adhesive to/through the adhesive to the electrical contacts or electrodes, 108, 109 and 110. Note, a corresponding one or more light apertures 111b/112b are shown in the adhesive of 113 of the example of FIG. 1D to communicate light therethrough in cooperation with the light conduit(s) 111a/112a in/through layer 105 for communication of light data typically involved in pulse oximetry and/or temperature sensing.

Further alternatives related to the adhesive may be used. In some implementations, a composite adhesive strip may be used having properties to reduce one or more motion artifacts. Typical ECG attachment systems use a conductive gel located over the electrode. Here, however, a hydrogel adhesive may be used which is embedded in a continuous sheet of laminated adhesives that cover the selected regions or the entire footprint of the device. The fact that the hydrogel itself has strong adhesive properties coupled with the complete coverage of the device with adhesives may assure a strong bond between the device and the patient's skin. Contributing to motion artifact reduction may be an alternative vertical placement of the device on the sternum which results in reduced motion artifacts for one or more of ECG signals, photoplethysmography waveforms, and oxygen saturation signals.

The devices and systems and methods hereof typically employ a technique referred to as "Reflectance Pulse Oximetry" to obtain O2Sat data from the strip device. In many implementations hereof, two wavelengths of light are shined onto and into the skin and into the capillary bed, then reflected back to the photodiode sensor. These reflected wavelengths are then used to calculate O2sat. On the other hand, many industry standard devices employ "Transmissive Pulse Oximetry" whereby the light is transmitted through an appendage, through the capillary bed, and into a photodiode sensor located on the opposite side of the appendage. The transmitted light is therein used for calculating oxygen saturation.

There are inherent challenges associated with the Reflectance method. One, which is addressed here, is referred to as "Venous Shift", and has been previously-identified and been the subject of numerous publications by others.

Figure 2A:
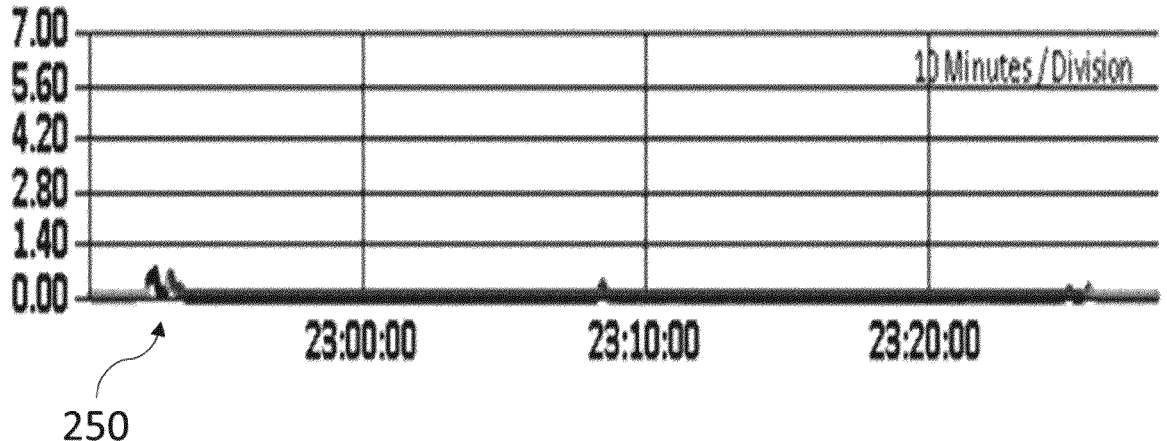
FIGS. 2A-2I illustrate "venous shift" (2A-2D) and a method to mitigate this venous shift (2E-2I).
Figure 2B:
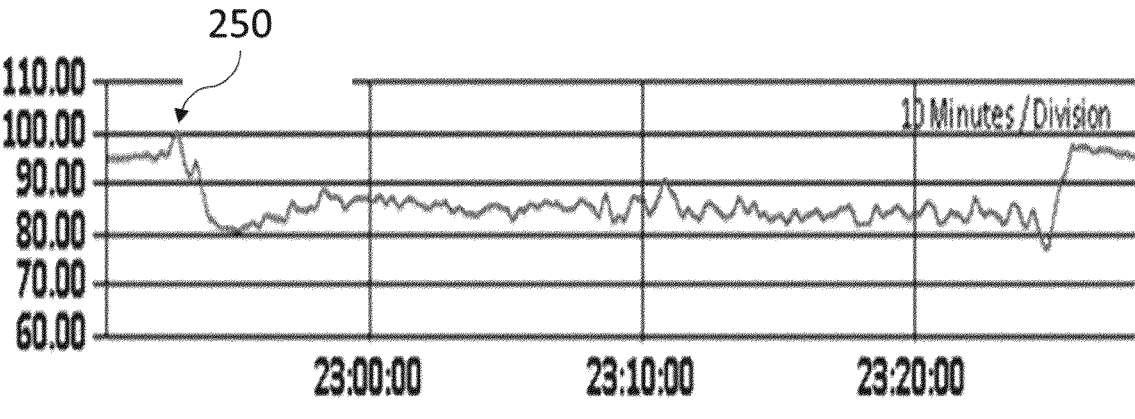

The "Venous shift" manifests itself as the sudden decrease in derived O2Sat values that occur occasionally when a test subject turns from a supine position to a position on either their left or right side. FIGS. 2A and 2B provide a good example of the 'Shift' (aka "Incorrect Oxygen Saturation due to Venous Shift"). In these examples of the shift, the subject is lying supine, then turns to his/her right side. Immediately the O2Sat appears to drop from ~95% to ~80% (blips in activity signal—arbitrary unit—versus time of FIG. 2A showing the activity, with the corresponding FIG. 2B showing concurrently the drop in apparent O2Sat in % versus time at the relevant point 250 previous to time point 23:00:00—point 250 shown in corresponding FIGS. 2A and 2B).

Figure 2C:
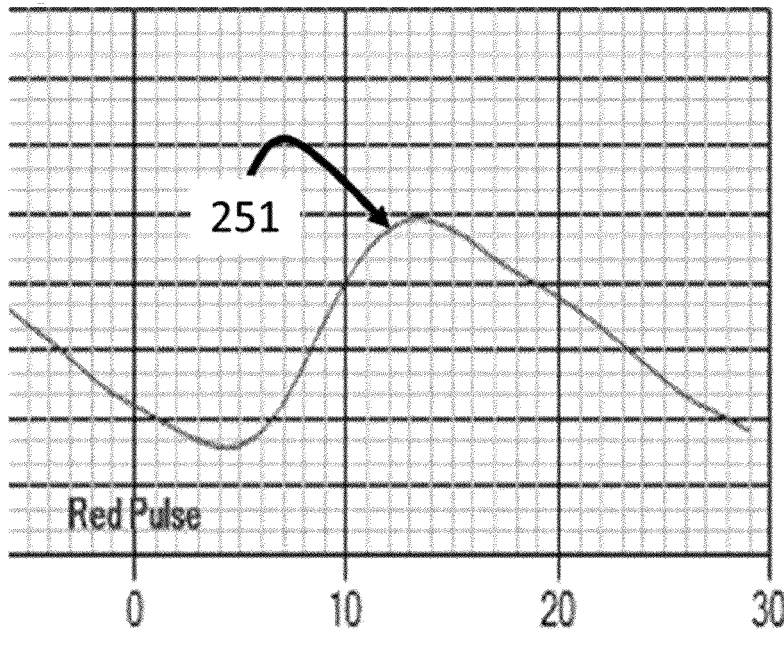
Figure 2D:
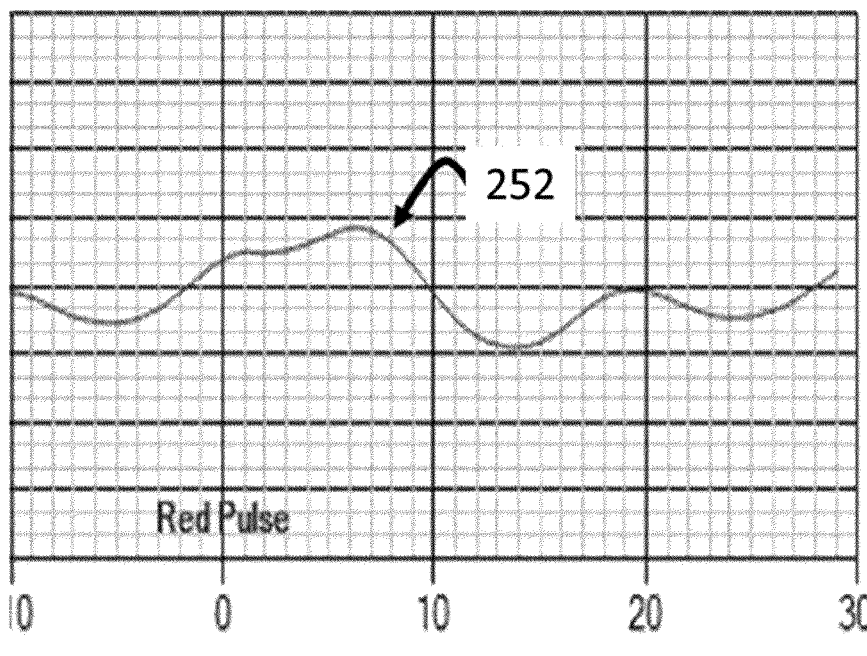

The "Venous shift" may also manifest itself in the raw PPG waveforms as shown in FIGS. 2C and 2D. The waveform 251 of FIG. 2C is substantially normal, where the waveform 252 of FIG. 2D is shifted. In other words, FIG. 2C shows a single arterial pulse normal PPG waveform 251 that produces a substantially accurate SpO2. However, FIG. 2D shows a contrary single arterial and venous pulse 252 that produces an inaccurate SpO2.

This "Venous shift" denotes the contribution of venous capillaries to light absorption which is then measured by the optical sensor and appears in photoplethysmograms. Herein, the contribution of venous capillaries in a photoplethysmogram is defined as follows. Raw PPG waveform is a superposition of light absorption correlated to arterial pulses—periodic and regular increase of arteria volume for each heart beat—whose regularity is governed by heart beats and light absorption correlated to venous flow without time correlation with heart beats and which appears equivalent to a white noise. The ratio defined as the intensity of equivalent white noise divided by the intensity of the PPG waveform is the contribution of venous capillaries.

Alternatively, contribution of venous capillaries may be derived from Fourier transform of PPG waveforms. Indeed, Fourier factors associated to the heart beat frequency (and its multiples) correspond to periodic signal of interest, i.e., arterial contribution, whereas other Fourier factors are associated to non-periodic signal to be filtered out, i.e., venous contribution. Thus, contribution of venous capillaries may be defined with the amplitude of Fourier coefficients associated to non-periodic signal.

Further, using signal processing methods, an algorithm can be run on the 'modified' PPG waveform 252 to transform the modified waveform 252 by removing the contribution of the venous waveform to a waveform that can be used to produce accurate SpO2 readings.

In methods to extract arterial pulse from Reflective PPG signal obfuscated by venous waveform—referred to as venous shift mitigation—to calculate SpO2 from PPG waveform, one must find the arterial pulses in the waveform, and using the Ratio of Ratios, the SpO2 can be calculated.

Figure 2E:
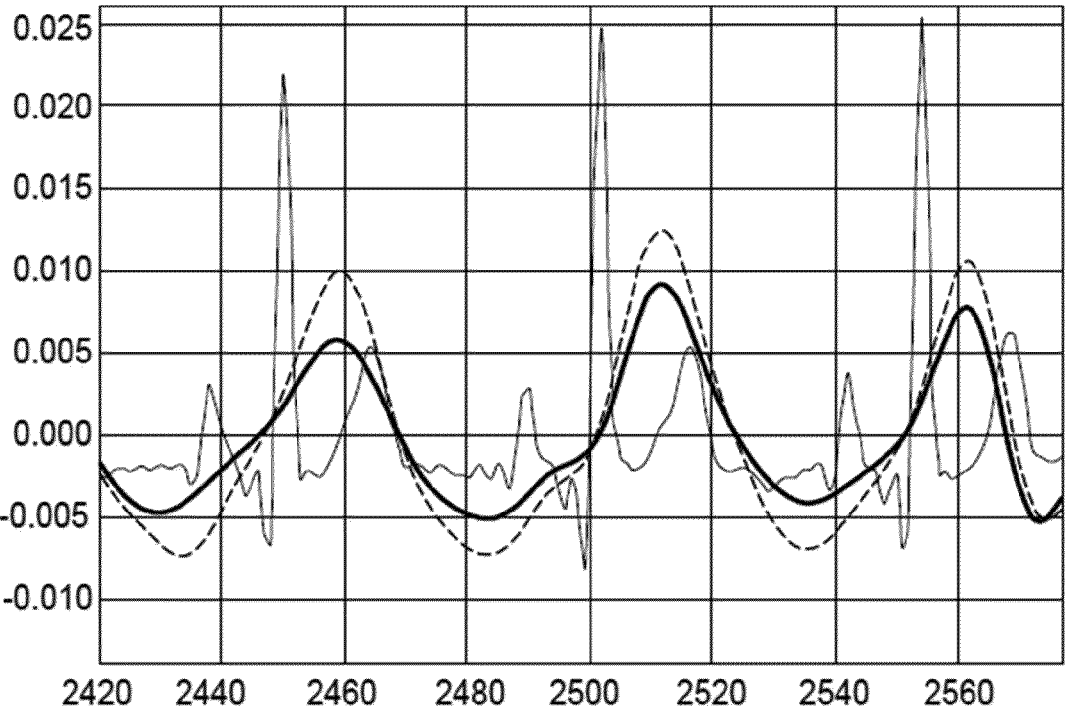

In FIG. 2E, the ECG is shown in light grey, while the red (bold solid line) and infrared (dotted line) PPG waveforms represent the arterial pulses. Note that there is a single pulse following each ECG QRS complex which is what one would expect. In FIG. 2E, PPG waveforms are almost periodic, and contribution of venous capillaries is estimated at about 5%. The distance from the ECG QRS and the peak of the PPG waveform is known as the Pulse Transit Time (PTT). The PTT is relatively constant for small changes in Blood Pressure, and can also be used to determine relative Blood Pressure.

Under certain conditions, this waveform can become distorted due to what is believed to be venous pooling, or a venous pulsatile waveform which combines with the arterial waveform, and this distortion results in a waveform that is not immediately conducive to deriving SpO2 from conventional methods.

Figure 2F:
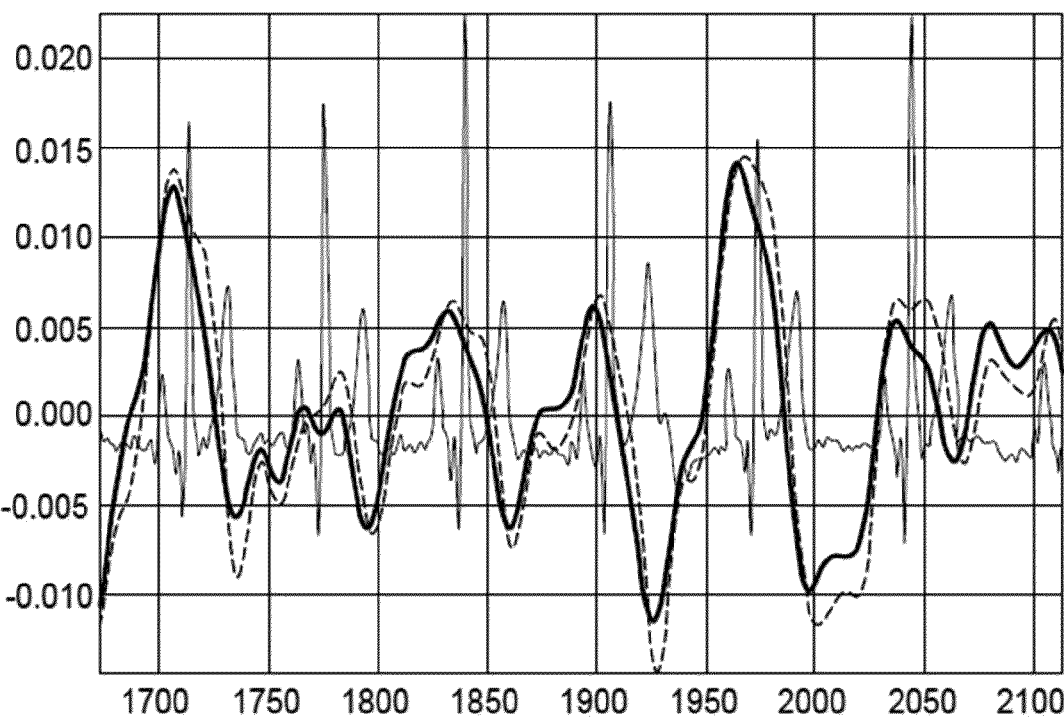

In FIG. 2F, one can see that the PPG signal is distorted, and the conventional method of deriving SpO2 would result in incorrect values. Indeed, PPG waveforms show a clear repetition of peaks almost synchronized on heart beats but strongly affected by random variations, and contribution of venous capillaries is estimated at about 50%. However, with devices and methods and systems hereof, which have simultaneous and synchronous capture of the ECG and PPG waveforms, it is possible to extract the correct true arterial pulse from this signal.

Figure 2G:
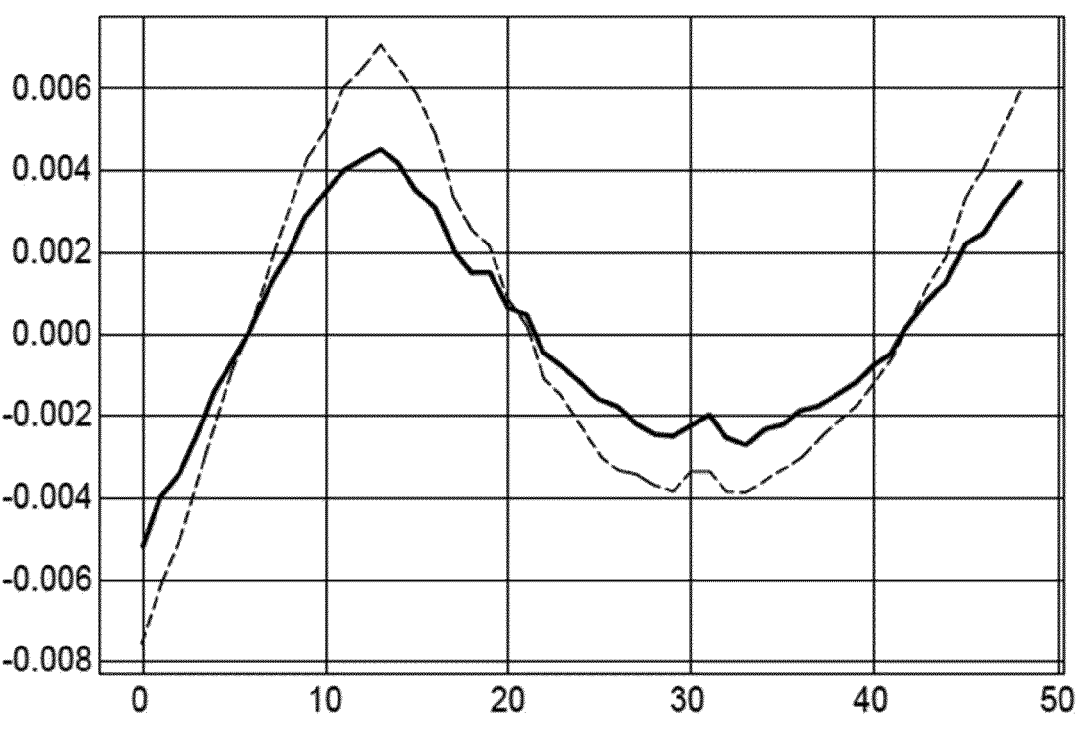

This is possible by knowing approximately where, in time referenced to the ECG QRS, the arterial pulse should exist. If one extracts a single pulse from the 2E, one can see the approximate timing of the peak of the arterial pulse. In FIG. 2G, the x axis time 0 is the firing of the ECG QRS complex—determined at the rising edge of Q wave—and the peak of the arterial pulse exists at approximately 12 units following that event. These units represent the sample rate of the PPG signal acquisition, and in this case, for one non-limiting example of 64 samples/second. So, 12 units would represent 12/64 of a second.

Figure 2H:
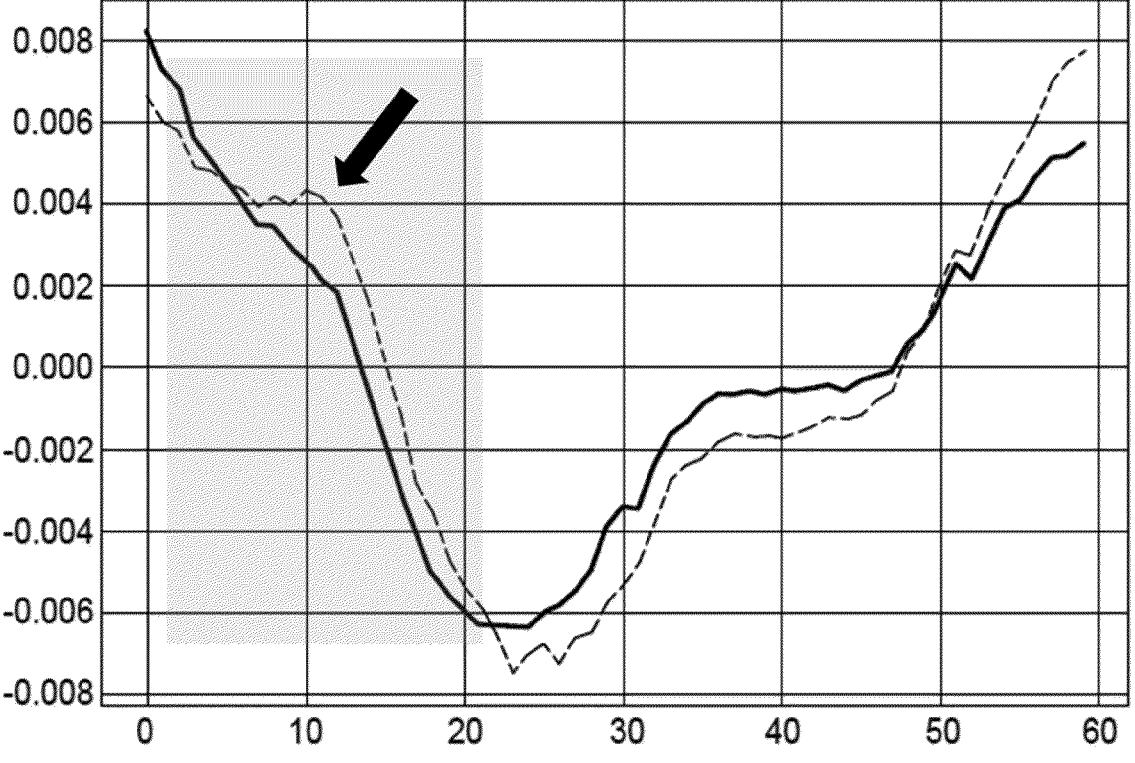

Using the 'framing' technique described hereinafter, one can form an average PPG waveform based on aggregating x frames using the ECG QRS as the starting point and some number less than the frequency of the heart rate as the ending point for each frame. Taking the distorted waveform from FIG. 2F and applying this technique, an aggregated waveform is obtained and shown in FIG. 2H.

When the PPG waveform is aggregated with this method, and knowing where the true pulsatile peak should exist relative to the ECG, (at approximately 12 units, highlighted with black arrow), the arterial pulse can be found. Taking this one step further, if one isolates just the portion of the signal in the grey-shaded rectangle inserted in the drawing FIG. 2H, and applying signal processing techniques, a signal more typical of the arterial pulse is obtained, as shown in FIG. 2I.

Figure 2I:
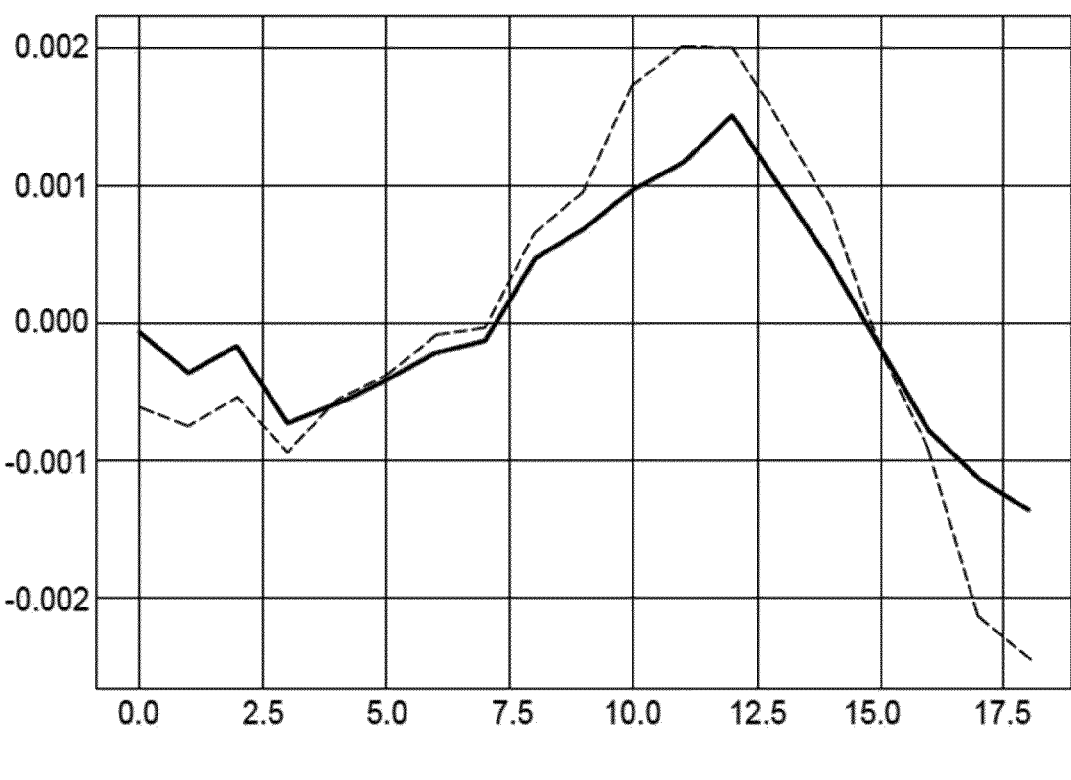

The signal in FIG. 2I represents the true arterial pulsatile signal taken from the distorted waveform shown in FIG. 2F. Note that the peak occurs at approximately 12 units, where we would expect it in this case as shown from FIG. 2G. This signal can then be used in the normal Ratio of Ratios computation to obtain the correct SpO2 value as desired.

This approach may be implemented by determining approximately where in time referenced to an ECG QRS, an arterial pulse waveform existing therein; the determining further including extracting a single arterial pulse from the arterial pulse waveform including first and second pulse waveforms from first and second wavelengths of light for that single arterial pulse, and finding the approximate timing of the peak of the single arterial pulse; establishing the x axis time 0 is the firing of the ECG QRS complex, and the peak of the single arterial pulse exists at approximately n units following that event, these units representing a sample rate of PPG signal acquisition; using a 'framing' technique, forming an average PPG waveform based on aggregating x frames using the ECG QRS as the starting point and some number less than the frequency of the heart rate as the ending point for each frame; taking a distorted waveform and applying this framing technique, developing an aggregated waveform; aggregating waveforms, and knowing where the true pulsatile peak should exist relative to the ECG, at approximately n units), the arterial pulse can be found; isolating just a portion of the signal, and applying signal processing techniques, to generate a signal more typical of the arterial pulse; and using this signal in the normal Ratio of Ratios computation to obtain the correct SpO2 value.

Alternatively, this approach may be implemented by determining a single arterial pulse from an ECG QRS; the determining further including extracting a single arterial pulse from an arterial pulse waveform of the ECG QRS including first and second pulse waveforms from first and second wavelengths of light for that single arterial pulse, and finding the approximate timing of the peak of the single arterial pulse; establishing the x axis time 0 is the firing of the ECG QRS complex, and establishing the peak of the single arterial pulse as existing at approximately n units following that event, these units representing a sample rate of PPG signal acquisition; using framing, including forming an average PPG waveform based on aggregating x frames using the ECG QRS as the starting point and some number less than the frequency of the heart rate as the ending point for each frame; taking a distorted waveform and applying this framing, developing an aggregated waveform; aggregating waveforms, and knowing where the true pulsatile peak should exist relative to the ECG, at approximately n units), finding the arterial pulse; isolating just a portion of the signal, and applying signal processing techniques, to generate a signal more typical of the arterial pulse; and using this signal in the normal Ratio of Ratios computation to obtain the correct SpO2 value.

A multi-pronged solution is described here; however, the scope of coverage hereof may be to any one or more of the below-presented approaches whether considered together or separately. Note again, an implementation of the issue may arise when a patient is wearing a strip device hereof vertically on the sternum and he/she moves from supine position, see FIG. 5A, e.g., to his/her left or right side, the pectoral muscle tends to push the PPG sensor away from the skin, see FIG. 5B. When the sensor is not applying pressure to the capillary bed, both the de-oxygenated venous blood and the oxygenated arterial blood contribute to the "Ratio of Ratios" method of calculating Oxygen Saturation; see FIG. 5C. It is clear that the de-oxygenated signal from the uncompressed venous capillary will lower the Ratio of Ratio calculation and result in the lower and inaccurate O2Sat reading of ~80%.

FIG. 4A shows a placement of the device 500, 500a on the chest of a patient 1000; and FIG. 4B show a placement of the device 500, 500a on the back 1000a of the patient 1000, near, on or just below the nape 1000b of the neck 1000c.

In a first method, to counteract the loss of contact pressure, a novel adhesive design may be employed. Since venous capillaries are at a much lower pressure than arterial capillaries, they will compress before the arterial capillaries, resulting in arterial blood as the only component in the Ratio of Ratio calculation; see FIG. 5D. The adhesive 513—for instance a foam adhesive able to be compressed—and/or the substrate 503a is/may be "stepped" adjacent the pleat/hinge 503h to allow the PPG sensor 511 to be "proud" enough, to maintain pressure great enough, to compress only the venous capillaries. By "proud", it is meant that the PPG sensor protrudes from device substrate by a sufficient thickness—at least 0.1 mm, typically 0.5 mm—to compress patient's skin and veins. Devices comprising a stepped substrate or a stepped adhesive configured to be disposed on the substrate are especially suitable.

Figure 5B:
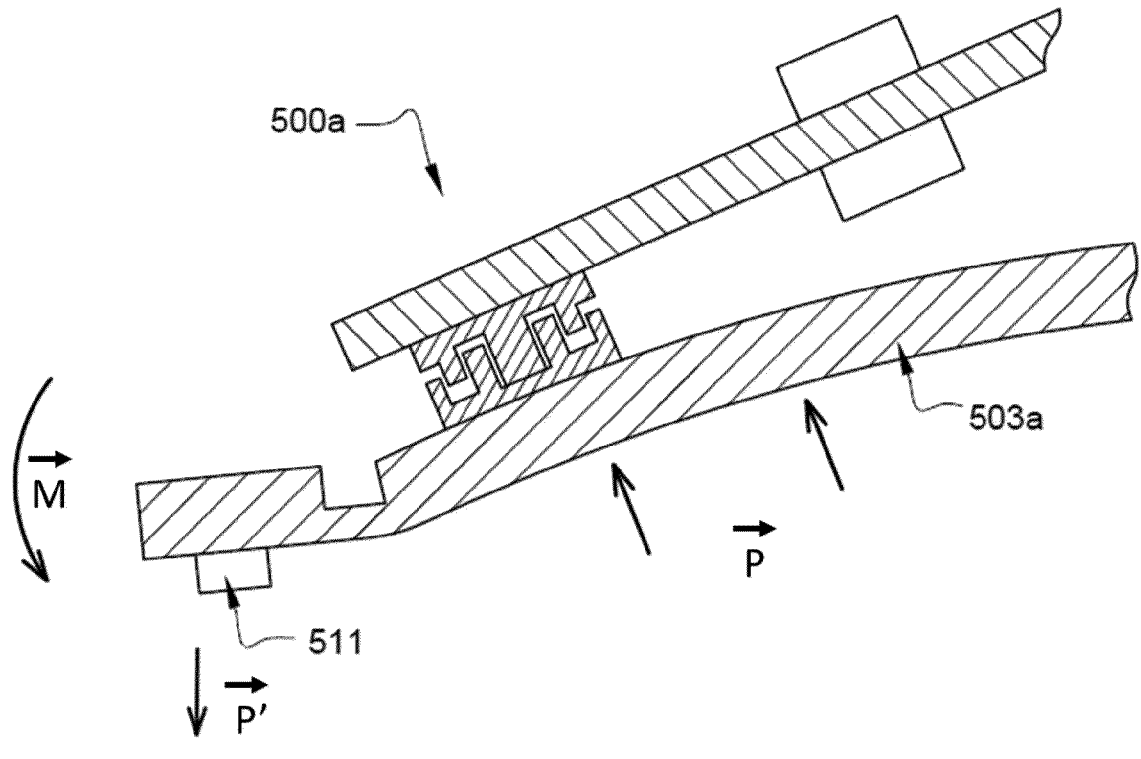
Figure 5C:
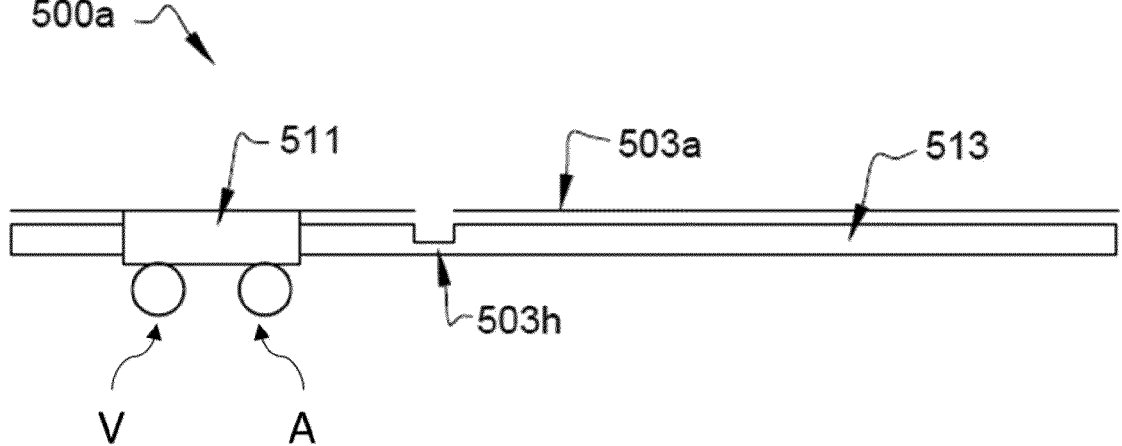
FIGS. 5C-D illustrate another embodiment of device allowing to mitigate venous shift by compression of venous capillaries.
Figure 5D:
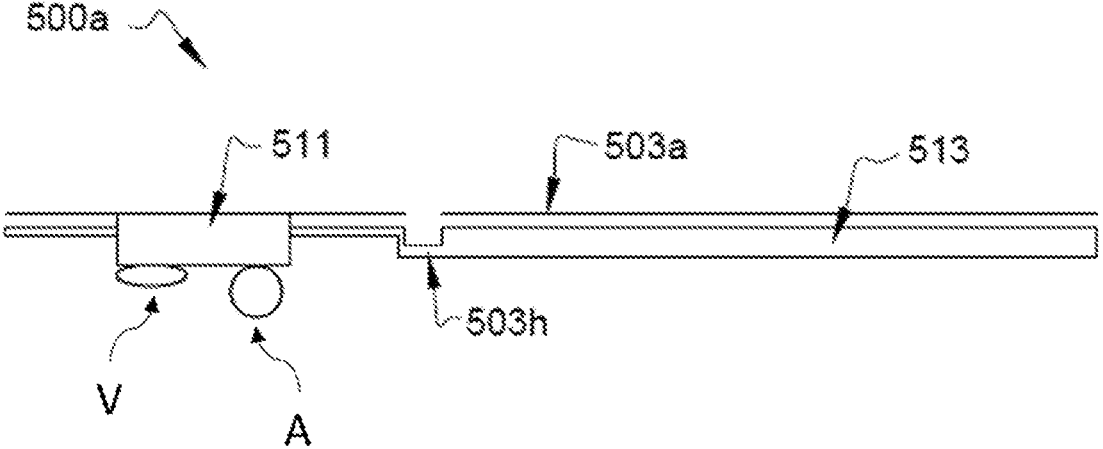

In a second method, applying pressure to the venous capillaries is achieved by placing the strip on a specific part of the body. For instance, strip may be placed horizontally on the sternum with the PPG sensor 511 on the sternum and the ECG electrode portion on the pectoral muscle. As the patient rolls over onto his side, the pleat/hinge allows the substrate 503a to bend as shown in FIG. 5B, applying a lever arm to the PPG sensor 511, and resulting in venous capillary compression.

Figure 4C:
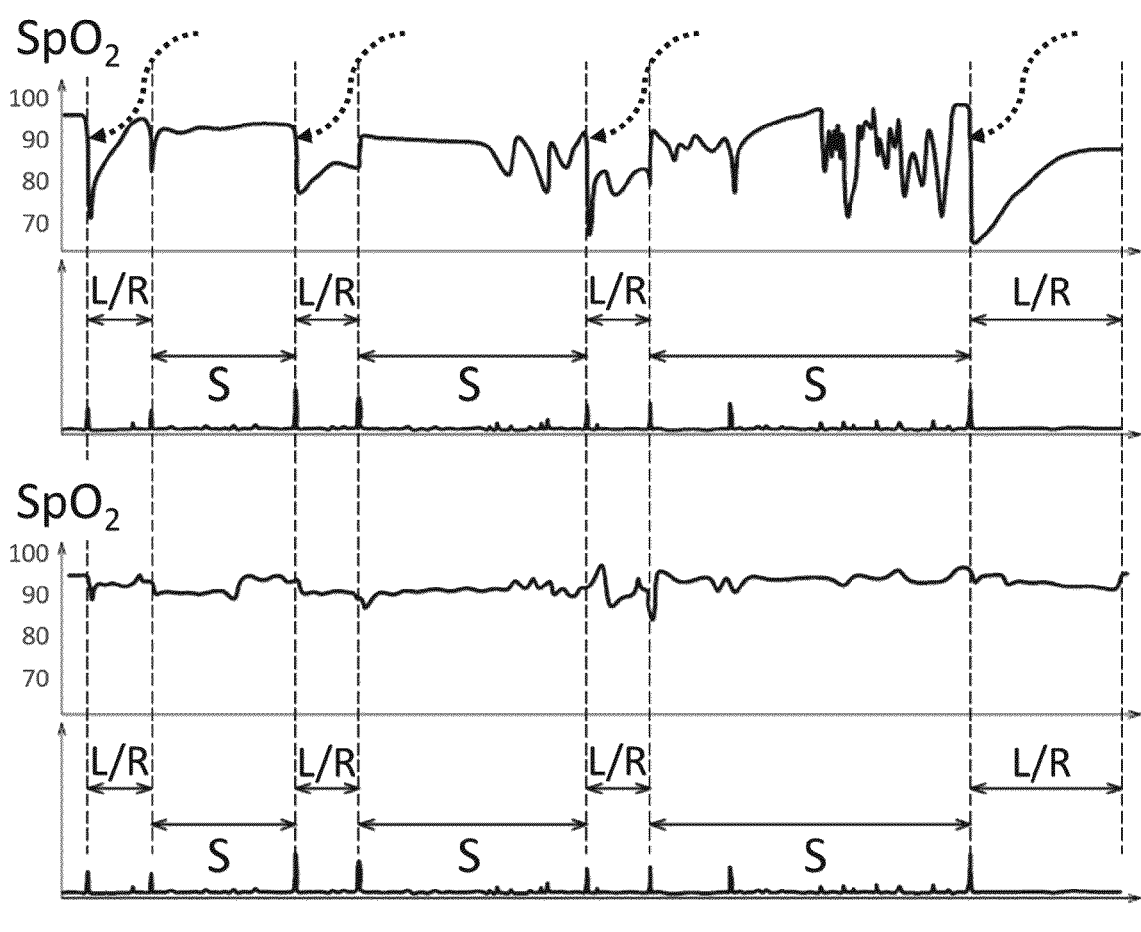
FIG. 4C compares SpO2 determination from a device placed on sternum (top) or on the back (bottom) of the patient.

Placing the device 500, 500a on the back of the subject, near the nape of the neck has some apparent and/or possible striking advantages over placement on or near the sternum on the front of the body; see FIG. 4A. For a first example, when the device 500, 500a is placed on the sternum and when the subject 1000 lies on his or her side, the pectoral muscles and fat tend to compress around the device. This leads to the veins in the capillary bed being filled with blood, skewing the PPG measurement. Accurate PPG measures depend upon arterial capillaries only. Along with mitigation methods outlined in the venous shift mitigation, placement of the device on the back as shown in the FIG. 4B has been shown to very effective and may perhaps even come close to eliminating venous capillaries from skewing PPG readings. FIG. 4C shows the SpO2 determination of an individual with two devices recording simultaneously physiological signals: first device is placed on sternum (top) and second device is placed on vertebra T1 of the neck (bottom). During acquisition, accelerometers record movements of the individual (peaks in arbitrary unit) and enable determination of actual position of the patient (supine noted S and lying on the side noted L/R). This position is shown below SpO2 signal, in time correspondence. Signal acquired on the sternum shows a shift (noted by dotted arrows on top graph), i.e., a lowering of SpO2 value, correlated to position on the side; the corresponding PPG waveform being represented in FIG. 2F. This artifact is almost eliminated with device placed on the back; the corresponding PPG waveform being represented in FIG. 2E. Because the muscles and fat of the back do not compress around the device as the pectoral muscles do, laying on one's side does not cause inaccurate PPG readings.

Looking at the experimental data, it is clear that the O2Sat reading is generally much flatter on the back than on the sternum, demonstrating the greater consistency of the back placement.

Advantageously, the device 500, 500a is placed near the nape of the neck. In addition, to improve light reflection, the PPG sensor is placed on a bone. By "on", it is here meant that the PPG sensor is placed so as to direct emitted light towards a bone, where it will be reflected. Placing the PPG sensor on the first thoracic vertebra (noted T1) yields especially good results with contribution of venous capillaries below 25%, typically below 10%.

As a further note, a remote ECG electrode 510 on a flexible tether 504 may be configured to be placed for best signal (not shown in FIG. 4A). When device 500, 500a is placed on the back, the tether 504 may be disposed to set the electrode 510 either on the front of the body over the shoulder, or on the back at a location chosen for best signal.

A third method involves signal processing techniques, first to identify if a shifted venous PPG waveform is occurring, and next to ameliorate its effects, allowing for an accurate Ratio of Ratios calculation.

As one can see from FIG. 2C. A 'good' PPG waveform 251 produces a single arterial pulse waveform which can be used to determine SpO2 using the Ratio of Ratios formulation. However, when the lower pressure venous pulse is added to the arterial pulse due to insufficient pressure applied by the sensor, a modified waveform is produced 252, FIG. 2D. Using signal processing techniques, this modified signal 252 can be detected as different from a standard PPG waveform 251 and the resultant derived SpO2 can be voided as inaccurate.

The method herein disclosed is especially suitable when it includes one or more of:

not compressing muscles or fat around the device;

not filling the veins in the capillary bed with blood, and/or not skewing a PPG or ECG reading; and/or flattening the O2 saturation reading.

In many implementations, a system hereof may include other circuitry operative together with the ECG electrodes, which may thus be accompanied by other sensors to provide time concordant traces of: i) ECG p-, qrs-, and t-waves; ii) PPG waveforms used to determine O2Sat, as measured by Pulse Oximetry; and/or iii) xyz acceleration, as measured by 3-Axis accelerometer, to provide an index of physical activity. Such circuitry may be implemented to one or more of the following electrical specifications. The overall system might in some implementations include as much as two weeks (or more) of continuous run time; gathering data during such time. Some implementations may be adapted to provide as many or even greater than 1000 uses. Alternatives may include operability even after or during exposure to fluids or wetness; in some such examples being water resistant, or waterproof, or watertight, in some cases continuing to be fully operable when fully submerged (in low saline water). Other implementations may include fast data transfer, as for an example where using an HS USB for full data transfer in less than about 90 seconds. A rechargeable battery may typically be used.

A further alternative implementation may include an electronic "ground": In a device hereof, mounted entirely on a flexible circuit board, the ground plane function may be provided by coaxial ground leads adjacent to the signal leads. The main contribution of this type of grounding system may be that it may allow the device the flexibility desired to conform and adhere to the skin. Note that this alternative implementation is not depicted in the drawings hereof.

For electrocardiograph; EKG or ECG, some implementations may include greater than about 10 Megohms input impedance; some implementations may operate with a 0.1-48 Hz bandwidth; and some with an approximate 256 Hz Sampling Rate; and may be implementing 12 Bit Resolution. For PPG and Pulse Oximeter, operation may be with 660 and 940 nm Wavelength; about 80-100 SpO2 Range; a 0.05-4.8 Hz Bandwidth; a 16 Hz Sampling Rate; and 12 bit resolution. For an accelerometer: a 3-Axis Measurement may be employed, and in some implementations using a ±2 g Range; with a 16 Hz Sampling Rate; and a 12 Bit Resolution. Some implementations hereof may operate with a 0.1-48 Hz bandwidth, and some with an approximate 256 Hz Sampling Rate; and may be implementing 24-bit resolution. Using an A/D converter with 24 bits may represent an approximately 60 dB gain in dynamic range, and may reduce the possibility of "saturating" or "railing" the amplifier and thus reducing errors or loss of signal issues that may have been generated by the PPG if only 12 bit resolution is used.

In some implementations, two electrodes may be used instead of the often conventional three, the third electrode here, e.g., 510 of FIG. 1G being optional; 508 and 509 being more primary. A conventional T1 chip is one way to achieve same; TI being Texas Instruments Corporation. Another option is from Microchip Corporation (Corporate Office 2355 West Chandler Blvd. Chandler, AZ 85224-6199), PIC24FJ1024GA610/GB610 FAMILY 16-Bit Microcontrollers with Large, Dual Partition Flash Program Memory and USB On-The-Go (OTG). To do so, two oscillators, provides for analysis of two ECG and one PPG on one chip, thus always in synchronicity (AFE device). Three electrodes are more difficult for a couple of reasons, including e.g., could cause blisters on the skin, particularly with a driven electrode. Temperature sensor, piezo microphone and accelerometer, may also be measured in synchronicity using the internal oscillator of microprocessor. Also allows more options, not just the removal of the third electrode; have choice of electrodes, physiological difference (skin color as above), Automatic gain control, for PPG, adjust for skin color, other sensitivities. 24 bits vs our prior 10 bits, we have control over the gain, and DC offset, the TI chip allows to DC, vs, ripple.

Figure 3:
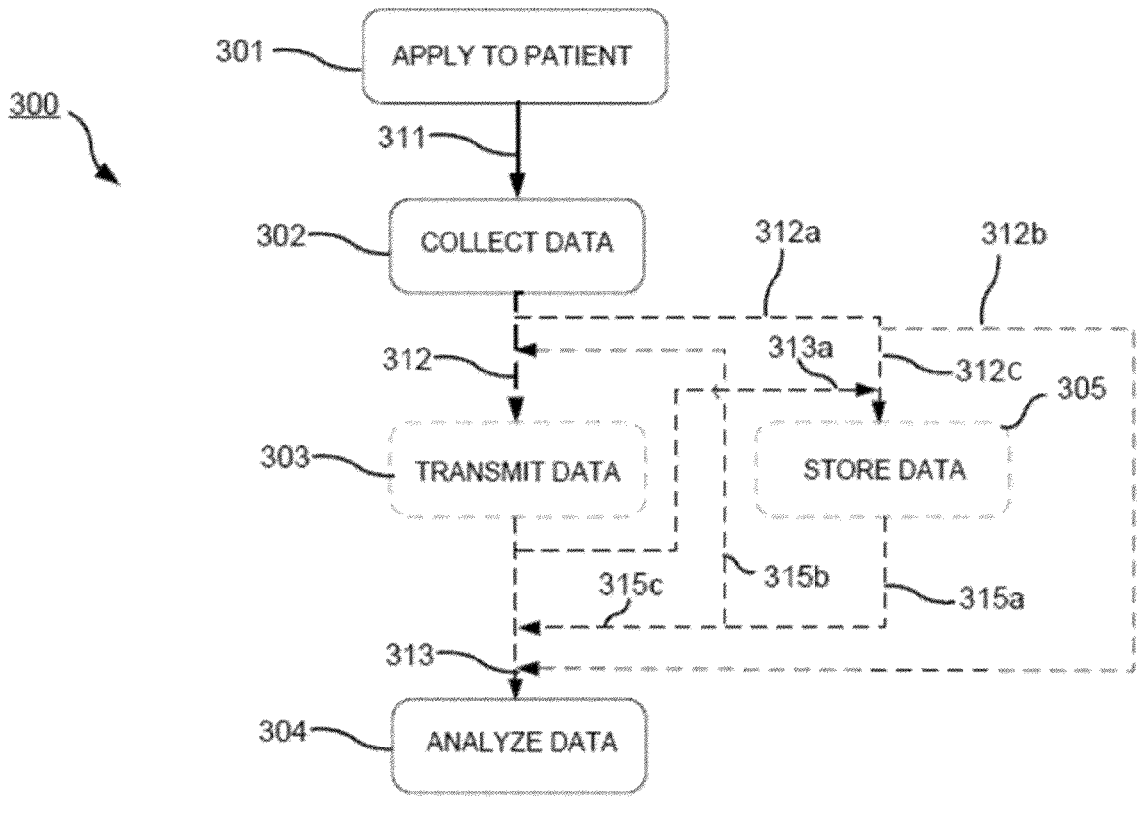
FIG. 3 is a flow chart including alternative methods of use.

Some summary methodologies may now be understood with relation to FIG. 3, though others may be understood through and as parts of the remainder of the disclosure hereof. A flow chart 300 as in FIG. 3 may demonstrate some of the alternatives; where an initial maneuver 301 might be the application of the device 100 to the patient. Then, as shown, in moving by flow line 311, a data collection operation 302 may be implemented. Note, this might include a continuous or substantially continuous collection or an interval or periodic collection or perhaps even a one-time event collection. This may depend upon the type of data to be collected and/or be dependent upon other features or alternatives, as for example whether a long-term quantity of data is desired, for ECG for example, or whether for example a relative single data point might be useful, as in some cases of pulse oximetry (sometimes a single saturation point might be of interest, as for example, if clearly too low, though comparison data showing trending over time, may indeed be more typical).

Several alternatives then present in FIG. 3, flow chart 300; a first such might be the following of flowline 312 to the transmission of data operation 303, which could then involve either wireless or wired (e.g., USB or other) data communication from the device 100 to data analysis and/or storage devices and/or systems. Options from this point also appear; however, a first such might include following flow line 313 to the data analysis operation 304 for analyzing the data for determination of the relative health and/or for condition diagnosis of a patient. Computing systems, e.g., a computer could be used for this analysis; however, it could be that sufficient intelligence might be incorporated within the electronics 103 of device 100 such that some analysis might be operable on or within device 100 itself. A non-limiting example, might be a threshold comparison, as for example relative to pulse oximetry where when a low (or in some examples, perhaps a high) threshold level is reached an indicator or alarm might be activated all on/by the electronics 103 of the device 100, or alternatively communicated wirelessly to a cellphone or tablet computer to alert the user.

A similar such example, might be considered by the optional alternative flow path 312a which itself branches into parts 312b and 312c. Following flow path 312 a, and then, in a first example path 312*b*, a skip of the transmit data operation 303 can be understood whereby analysis 304 might be achieved without substantial data transfer. This could explain on board analysis, whether as for example according to the threshold example above, or might in some instances include more detailed analysis depending upon how much intelligence is incorporated on/in the electronics 103. Another view is relative to how much transmission may be involved even if the transmission operation 303 is used; inasmuch as this could include at one level the transmission of data from the patient skin through the conductors 108, 109 and/or 110 through the traces 107 to the electronics 103 for analysis there. In other examples, of course, the transmission may include off-board downloading to other computing resources. In some cases, such off-loading of the data may allow or provide for more sophisticated analysis using higher computing power resources.

Further alternatives primarily may involve data storage, both when and where, if used. As with intelligence, it may be that either some or no storage or memory may be made available in/by the electronics 103 on-board device 100. If some storage, whether a little or a lot, is made available on device 100, then, flow path 312*a* to and through path 312*c* may be used to achieve some storing of data 305. This may in many cases then, though not necessarily be before transmission or analysis (note, for some types of data multiple paths may be taken simultaneously, in parallel though perhaps not at the same time or serially (e.g., paths 312*b* and 312*c* need not be taken totally to the exclusion of the other), so that storage and transmission or storage and analysis may occur without necessarily requiring a completion of any particular operation before beginning or otherwise implementing another). Flow path 313*a* shows data storage after transmission. Thus, after (or during) storage 305, flow path 315*a* may be followed for stored data which may then be transmitted, by path 315*b* to operation 303, and/or analyzed, by path 315*c* to operation 304. In such a storage example, which in many cases may also be an on-board storage example, data can be collected then stored in local memory and later off-loaded/transmitted to one or more robust computing resources for analysis. Frequently, this can include long term data collection, e.g., in the manner of days or weeks or even longer, and may thus include remote collection when a patient is away from a doctor's office or other medical facilities. Thus, data can be collected from the patient in the patient's real-world circumstances. Then, after collection, the data can be transmitted from its storage on device 100 back to the desired computing resource, and such transmission might be wireless or wired or come combination of both, as for example a Bluetooth or Wi-Fi connection to a personal computer which might then communicate the data over the internet to the designated computer for final analysis. Another example might include a USB connection to a computer, either to a PC or a mainframe, and may be to the patient computer or to the doctor computer for analysis.

For example, an electrocardiogram trace that reveals a ventricular arrhythmia during intense exercise may be interpreted differently than the same arrhythmia during a period of rest. Blood oxygen saturation levels that vary greatly with movement can indicate conditions that may be more serious than when at rest, inter alia. Many more combinations of the four physiologic parameters are possible, and the ability of software hereof to display and highlight possible problems will greatly aid the physician in diagnosis. Thus, a system as described hereof can provide beneficial data interpretation. Some of the features which can assist toward this end may be subsumed within one or more of operations 303 and 304 of FIG. 3, wherein data collected on a device 100 can rather simply be communicated/transmitted to computing resources (again, whether on-board device 100 or discrete therefrom). For an example, when a patient having had a device applied (operation 301) may return to a physician's office after a test period wherein data was collected (operation 302) the device is connected via one or more data transmission alternatives, as for example, USB to a computer (Windows or Mac) in the office, allowing immediate analysis by the physician while the patient waits (note, the device 100 may first have been removed from the patient or might remain thereon pending transmission and analysis for determination of whether more data may be desired). In some implementations, data analysis time may be relatively quick, at approximately less than 15 minutes, less than 10 minutes, and less than 5 minutes in some implementations, and might be achieved with a user-friendly GUI (Graphic User Interface) to guide the physician through the analysis software.

The analysis/software package may be disposed to present the physician with results in a variety of formats. In some implementations, an overview of the test results may be presented, either together with or in lieu of more detailed results. In either case, a summary of detected anomalies and/or patient-triggered events may be provided, either as part of an overview and/or as part of the more detailed presentation. Selecting individual anomalies or patient-triggered events may provide desirable flexibility to allow a physician to view additional detail, including raw data from the ECG and/or from other sensors. The package may also allow data to be printed and saved with annotations in industry-standard EHR (Electronic Health Record) formats.

As mentioned above, in one aspect of the developments hereof, ECG signals collected in time concordance with pulse oximetry signals may be used to reduce the noise in the pulse oximetry signals and to permit the calculation of values for oxygen saturation, particularly in circumstances where sensors pulse oximetry data are placed on noise-prone locations of a patient, such as the chest. This approach is referred to "framing" throughout this disclosure. In some implementations, this aspect may be implemented by the following steps: (a) measuring an electrocardiogram signal over multiple heart beats; (b) measuring one or more pulse oximetry signals over multiple heart beats such that the electrocardiogram signal and the one or more pulse oximetry signals are in time concordance over one or more heart beats; (c) comparing a portion of the electrocardiogram signal and the one or more pulse oximetry signals in time concordance over one or more heart beats to determine a constant component and a primary periodic component of each of the one or more pulse oximetry signals; and (d) determining oxygen saturation from the constant components and primary periodic components of the one or more pulse oximetry signals. Measurement of the ECG signals and pulse oximetry signals may be implemented by implementations of devices hereof. In particular, pulse oximetry signals may be a reflective infrared signal and a reflective red-light signal collected by a photodetector in a device hereof. Alternatives may include other colors, as for example green in addition to or in lieu of one or both of red and infrared. Such alternatives are described further below.

Intervals of pulse oximetry signals corresponding to heart beats may be determined by comparing such signals to the time concordant ECG signals. For example (not intended to be limiting), successive R-wave peaks of a time concordant ECG signal may be used to identify such intervals, although other features of the ECG signal may be used as well. Once such intervals are identified, values at corresponding times within the intervals may be averaged to reduce signal noise and to obtain more reliable values for the constant components (sometimes referred to as the "DC components") and the main periodic components (sometimes referred to as the "AC components") of the pulse oximetry signals, e.g., Warner et al, Anesthesiology, 108:950-958 (2008). The number of signal values recorded in an interval depends on the signal sampling rate of the detectors and processing electronics employed. Also, as the intervals may vary in duration, the averaging may be applied to a subset of values in the intervals. As described below, oxygen saturation values may be computed from such DC and AC components using conventional algorithms. The number of heart beats or intervals over which such averages may be computed may vary widely, as noted below. In some implementations, signals from one or more heart beats or intervals may be analyzed; in other implementations, signals from a plurality of heart beats or intervals may be analyzed; and in some implementations, such plurality may be in the range of from 2 to 25, or in the range of from 5 to 20, or in the range of from 10 to 20.

As described, a method of pulse oximetry measures photoplethysmogram (PPG) signals at red and infrared wavelengths. The DC or mean value is estimated and subtracted, and the ratio of AC or pulsatile signal is estimated and/or averaged. Linear regression between the two signals can be used as described below. However, performance is limited because similar noise exists in both the red and infrared signals. Photoplethysmography taken using green light (~550 nm) is more resilient to motion noise because the light is absorbed much more by blood than by water or other tissue. However, the difference between oxygenated and deoxygenated blood in the green region of the spectrum is much less than red. In an alternative, a green PPG signal (or long-time average of red/infrared (see below)) may be used to determine the shape of the pulsatile signal. A weighted average of any number of different wavelengths (such as green, red and infrared) may be used to estimate the shape of the pulsatile waveform.

ECG or green PPG (or like) or long-time average of red/infrared (see below) data may be recorded in time-concordance with two or more photoplethysmograms of different light wavelengths. The heart beats are detected in the ECG or green PPG signal. These heart beats allow for definition of a 'frame' of photoplethysmogram data for the time between two adjacent heart beats. Two or more of these frames can then be averaged together at each point in time to create an average frame for the time interval. Because the photoplethysmogram is correlated with the heartbeat, the photoplethysmography signal is reinforced by this averaging. However, any motion artifact or other noise source that is uncorrelated in time with the heartbeat is diminished. Thus, the signal-to-noise ratio of the average frame is typically higher than that of the individual frames.

Having constructed an average frame for at least two photoplethysmograms of different light wavelengths, linear regression can then be used to estimate the gain between the two average frame signals. This gain value may be used to estimate blood oxygen saturation information or other components present in the blood such as hemoglobin, carbon dioxide or others. The process may be repeated for additional and/or alternative light wavelengths in order to do so.

Exemplar/alternative methods hereof may include determining the gain between particular and/or discrete signals, as between the red and Infrared and/or green frame signals, if/when such may be used. These may be found by averaging the two frames together first. This may result in a signal with reduced noise. The gain is found by performing linear regression of the red versus combined and Infrared versus combined and then finding the ratio of these two results; or linear regression of the red versus combined with green and Infrared versus combined with green and then finding the ratio of these two results; or linear regression of red versus green and Infrared versus green and then finding the ratio of these two results; or by linear regression of combining green with each of red and Infrared and using the ratio of these results.

Another method involves selecting a possible gain value, multiplying the average frame signal by it, and determining the residual error with respect to an average frame of a different wavelength. This process may be repeated for a number of potential gain values. While simple linear regression finds the global minimum gain value, this method allows for finding local minima. Thus, if it is likely that the global minimum represents correlation caused by motion artifact, venous blood movement or another noise source, it may be ignored, and a local minimum may be selected instead.

Yet another method uses an ensemble average of the red and/or Infrared signals over a much longer time to determine the pulse waveform shape, then fitting shorter time averaged signals to that waveform shape. Basically, the green light signal or ECG signal described above may be replaced with a long-time average of red/Infrared.

As mentioned above, patient wearable devices hereof for implementing the above aspects may be particularly useful for monitoring oxygen saturation in noisy regions for such measurements, for example, where there is significant local skin movement, such as the chest location, or where there is significant contribution of venous capillaries to the PPG waveforms.

Figure 6A:
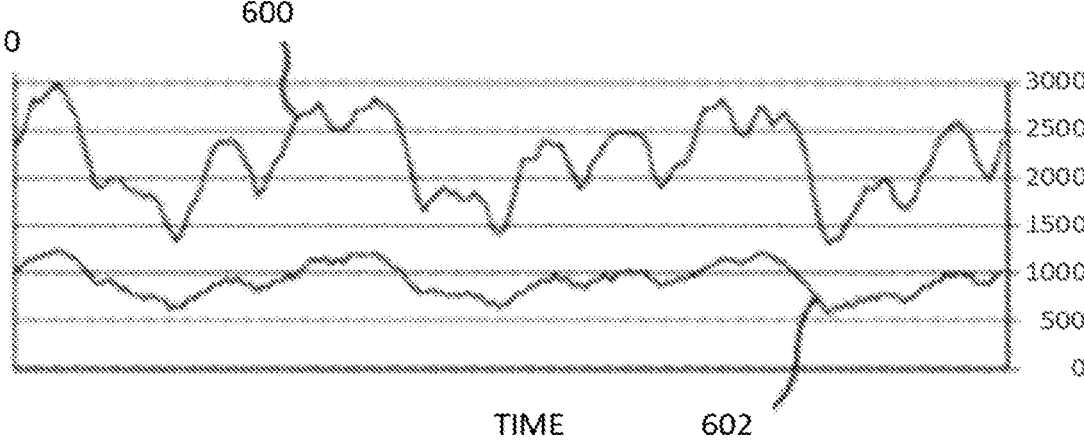
FIGS. 6A-B illustrate features of one embodiment for measuring SpO2 using synchronized ECG signal and PPG signal.
Figure 6B:
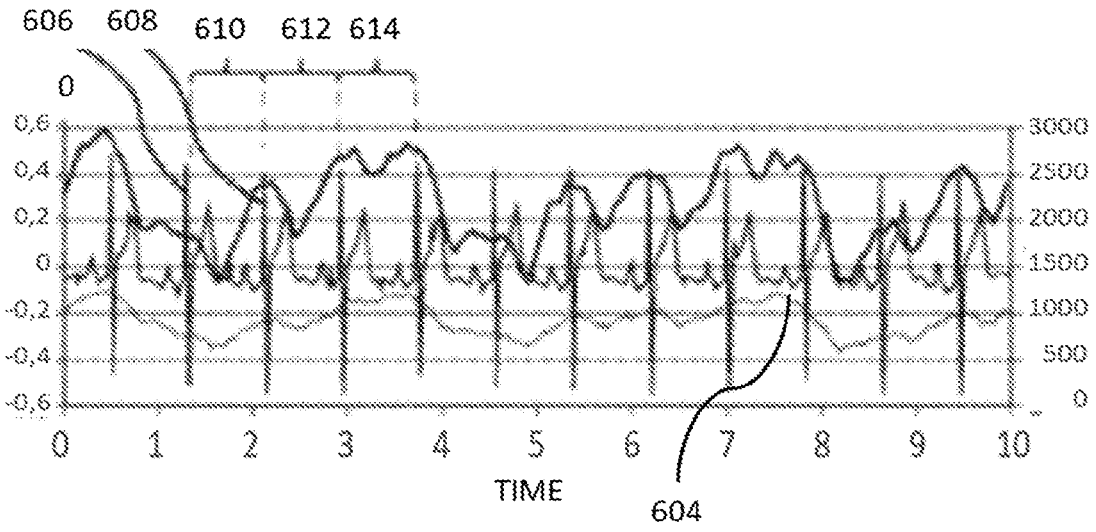
Figure 6C:
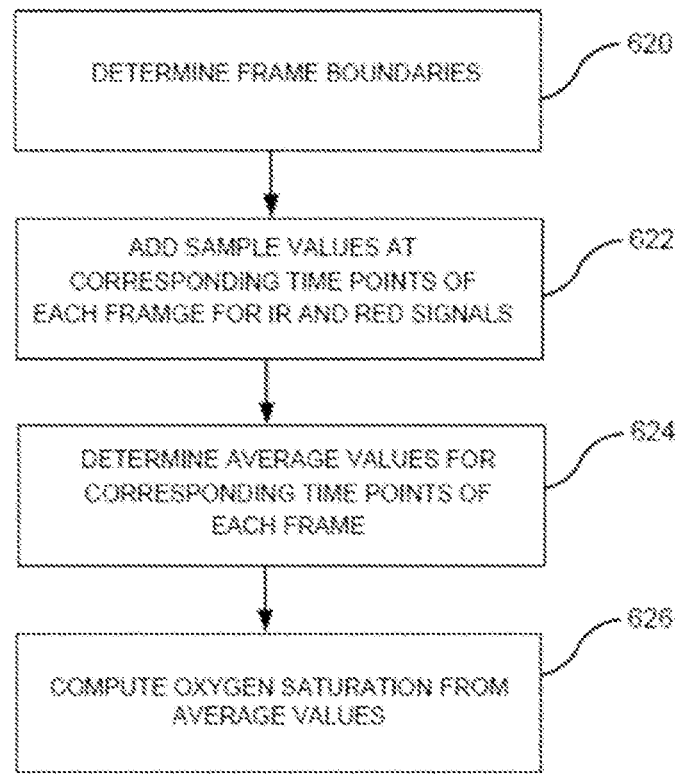
FIG. 6C is a flow chart showing an embodiment for determining SpO2.

One implementation of the above aspect hereof is illustrated in FIGS. 6A-6C. In FIG. 6A, curve A (600) illustrates time (in seconds) varying output of the photodiode (arbitrary unit) of a device hereof for infrared reflection and curve B (602) illustrates time varying output of the photodiode (arbitrary unit) of the device for red light reflection. In some implementations, the skin is alternatively illuminated by the red and infrared LEDs to generate the signals collected by the same photodiode. In FIG. 6B, time synchronized (i.e., time concordant) ECG data (or alternatively/additionally green PPG data or long-time average of red/infrared as introduced above), illustrated by curve C (604), is added to the plot of FIG. 6A. Peak values in the ECG data (e.g., peaks 606 and 608 may be used to define frames or intervals of pulse oximetry data. Additional consecutive frames or intervals are indicated by 610, 612 and 614, and further frames may be similarly determined. In accordance with this aspect, pulse oximetry data from a plurality of frames is collected. The magnitude of the plurality may vary widely depending on particular applications. In some implementations, the plurality of frames collected is from 5 to 25; in one implementation, a plurality is between 8 and 10 frames. Typically, frames or intervals of pulse oximetry data contain different numbers of signal samples. That is, output from the sensors may be sampled at a predetermined rate, such a 32 samples per second. If the time between ECG (or green PPG or long-time average of red/infrared) peaks varies, then the number of samples per frame will vary. In one implementation, features in the ECG (or green PPG or long-time average of red/Infrared) data serving as the starting points of a frame are selected so that an associated peak in the pulse oximetry data is approximately in the mid-point, or center, of the frame, after which a predetermined number of signal samples are recorded for each frame. Preferably in this implementation, the predetermined number is selected to be large enough to ensure that the pulse oximetry signal peak is roughly mid-frame. Sample values corresponding to time points above the predetermined value are not used. After a plurality of frames of data is collected, averages of the values at corresponding time points of the frames are computed. The values from such averages AC and DC components of the pulse oximetry data are determined and are then used to compute relative oxygen saturation by conventional methods, such as the ratio-of-ratios algorithm, e.g., Cypress Semiconductor document No. 001-26779 Rev A (Jan. 18, 2010). This basic procedure is summarized in the flow chart of FIG. 6C. First, frame size (in terms of number of samples) is determined (620). Next, values of samples at corresponding time points within each frame are summed (622), after which average values for each time point of each frame are computed (624) which, in turn, give the AC and DC components of Infrared and red and/or green light reflection with reduced noise. In some implementations, values for these components can be used to compute oxygen saturation using conventional algorithms (626). Relative values for oxygen saturation may be converted into absolute values by calibrating the measurements for particular implementations. Calibration may be carried out in controlled environments where individuals are exposed to varying atmospheric concentrations of oxygen and measured oxygen saturation values are related to corresponding oxygen levels.

In addition to the above implementation for comparing ECG and/or green PPG or long-time average of red/Infrared signals with pulse oximetry signals, a range of other implementations for such comparing is within the comprehension of those of ordinary skill in the art. For example, in order to find peaks of the AC component of pulse oximetry signals in the presence of noise, features of the time concordant ECG signal that are located at characteristic times preceding and succeeding the pulse oximetry maximum and/or minimum values may be used to reliably determine the pulse oximetry peak and minimum values when averaged over a plurality of heart beats (without the need to average all values of the pulse oximetry signal over the heart beats). For example, if, within an interval, the R wave peak of an ECG signal characteristically preceded a pulse oximetry signal maximum by x milliseconds and trailed a pulse oximetry signal minimum by y milliseconds, then the essential information about the AC component of the pulse oximetry signal may be obtained by repeated measurements of just two values of pulse oximetry signals.

In some implementations, heart beat timing (e.g., from ECG) and PPG signals can be used to determine pulse transit time; i.e., the time for the pressure wave to travel from the heart to other locations in the body. Measurements of pulse transit time may then be used to determine or estimate blood pressure. Note, the heartbeat timing, ECG and/or PPG signals may be generated by conventional or other to-be-developed methods, systems or devices, or may be developed by wearable devices such as those otherwise described herein. I.e., the algorithms hereof may be separately usable, as well as being usable in the wearable cardiac device.

As disclosed herein elsewhere, the PPG signals of several heart beats may be averaged by correlating each with a respective heartbeat. The result is a PPG frame where the heart rate-correlated PPG signal is reinforced while uncorrelated noise is diminished. Moreover, because the PPG frame is already correlated to the timing of the heartbeat, pulse transit time may be estimated by determining the location of either the peak or minimum with respect to either the beginning or end of the frame itself. This may be done either by finding the minimum and/or maximum sample(s), or by interpolating the signal to find points between measured samples. For example, interpolation may be done with a quadratic fit, a cubic spline, digital filtering, or many other methods.

The pulse transit time may also be estimated by correlating the PPG frame with a sample signal. By shifting the two signals with respect to each other, the time shift resulting in the maximum correlation may be determined. If the sample signal is an approximation of the expected PPG frame, then the time shift with maximum correlation may be used to determine the pulse transit time.

In all methods disclosed herein, Pulse Transit Time (also known as PTT) may also or alternatively be used as an indicator of error in PPG determination of Blood Oxygen. PTT is the measurement of the time it takes a pulse to travel from the heart to a sensor placed at some distance from the heart on a subject's body. PTT is commonly used as a surrogate for the relative measurement of systolic blood pressure on wearable devices that provide both ECG and PPG waveforms. When the PPG waveform is modulated by other non-arterial waveforms such as motion or venous capillaries artifacts, the waveform can become very unstable resulting in an incorrect determination of Blood Oxygen. Thus, a measurement of PTT stability over time can be used as a technique to determine the confidence level of derived Oxygen levels.

Figure 2J:
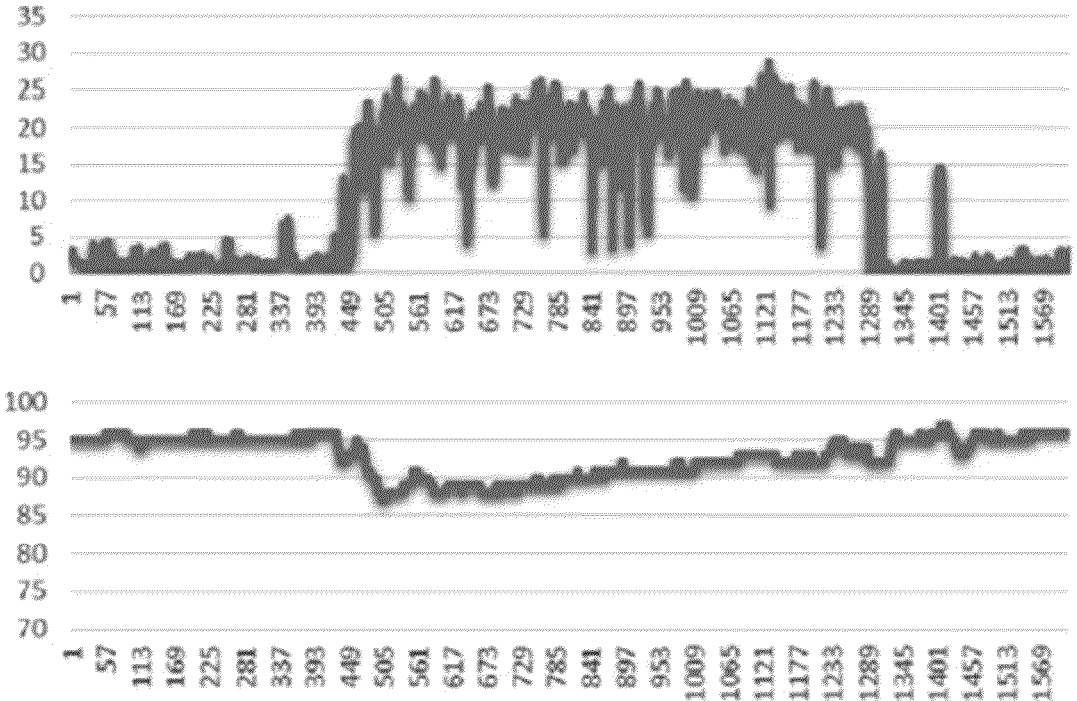
FIG. 2J shows standard deviation of Pulse Transit Time (PTT, unit is time sampling period, here 1/64 second) versus time (in seconds) on top and corresponding SpO2(%) versus time on bottom.

In normal function the pulsatile waveform is relatively static in terms of shape and arrival time at the measurement site. However, when the PPG waveform is modulated by other non-arterial waveforms such as motion or venous vasculature artifacts, the waveform can become very unstable resulting in an incorrect determination of Blood Oxygen. Because of this, a measurement of PTT stability over time can be used as a technique to determine the confidence level of derived Oxygen levels also known as SpO2. Below shows a demonstration of this technique where the stability of the PTT, as determined by the standard deviation of the PTT over as short time period is indicative of the error in the derived Oxygen Levels. In FIG. 2J, a deviation from normal is shown in standard deviation of PTT at about the horizontal marker 449 until a short bit after about the horizontal marker point 1289. In the corresponding SpO2 curve, a deviation in the oxygen determination is shown corresponding at points 449 to a short bit after about 1289. Thus, the PTT standard deviation is indicative of an error in the oxygen determination, an error that can be signaled or otherwise communicated or used in reporting the SpO2 concentration.

In order to implement the use of Pulse Transit Time as an indicator of error in PPG determination of SpO2, a three-step method may be implemented. In a first step, Pulse Transit Time is determined from time concordant electro-cardiogram and photoplethysmogram for each heartbeat. Then, the standard deviation of Pulse Transit Time is computed over a period comprising between 10 and 45 heart beats—corresponding to a time between 10 s and 30 s for usual heart rates. Last, when standard deviation of PTT exceeds a threshold, a confidence level is issued with SpO2 determination. The confidence level may take several values depending on the value of standard deviation of PTT and/or duration of standard deviation of PTT being higher than determined threshold. As PTT depends on blood pressure and exact location of sensors, it varies broadly from one patient to another. Therefore, the threshold has to be predetermined for each patient. For instance, PTT may be measured during a short calibration period yielding the average value and standard deviation of PTT. Then, the threshold may be determined as a function of PTT standard deviation measured during calibration.

Figure 7A:
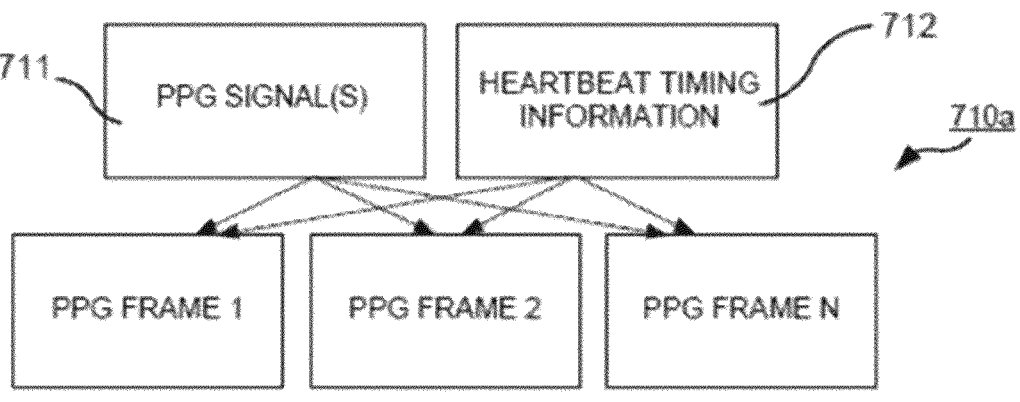
FIGS. 7A-C are flow diagrams for alternative embodiments for determining SpO2.
Figure 7B:
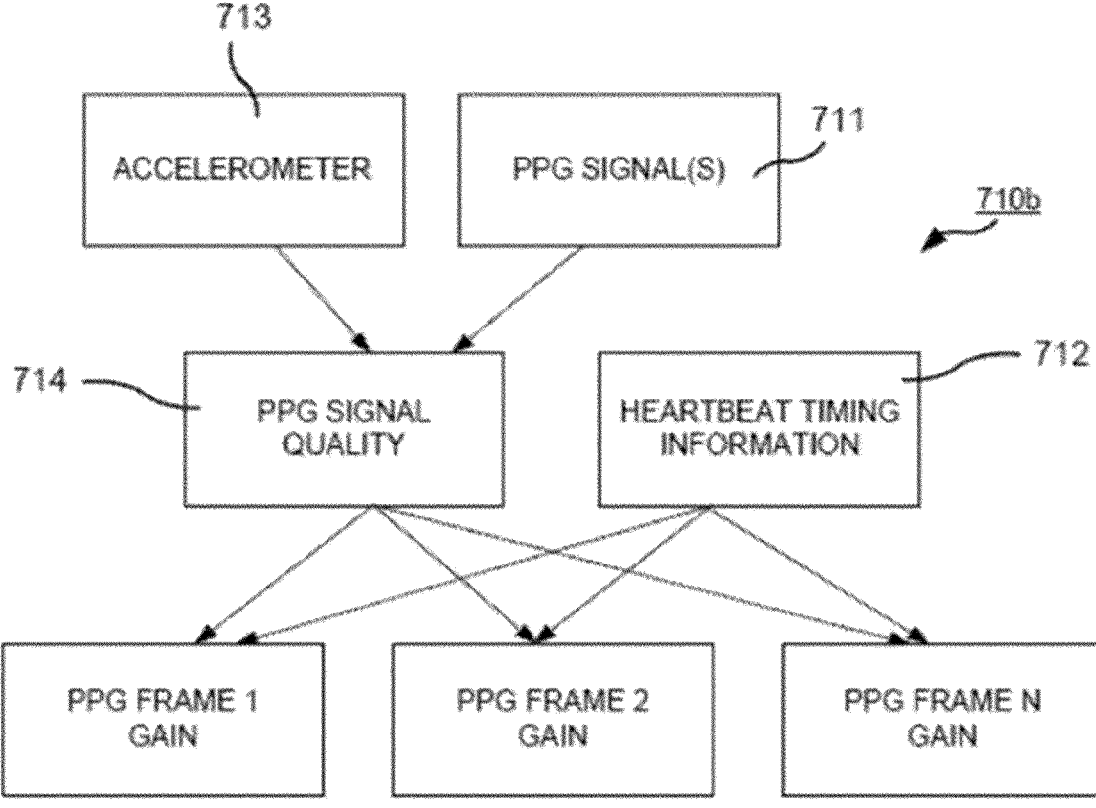
Figure 7C:
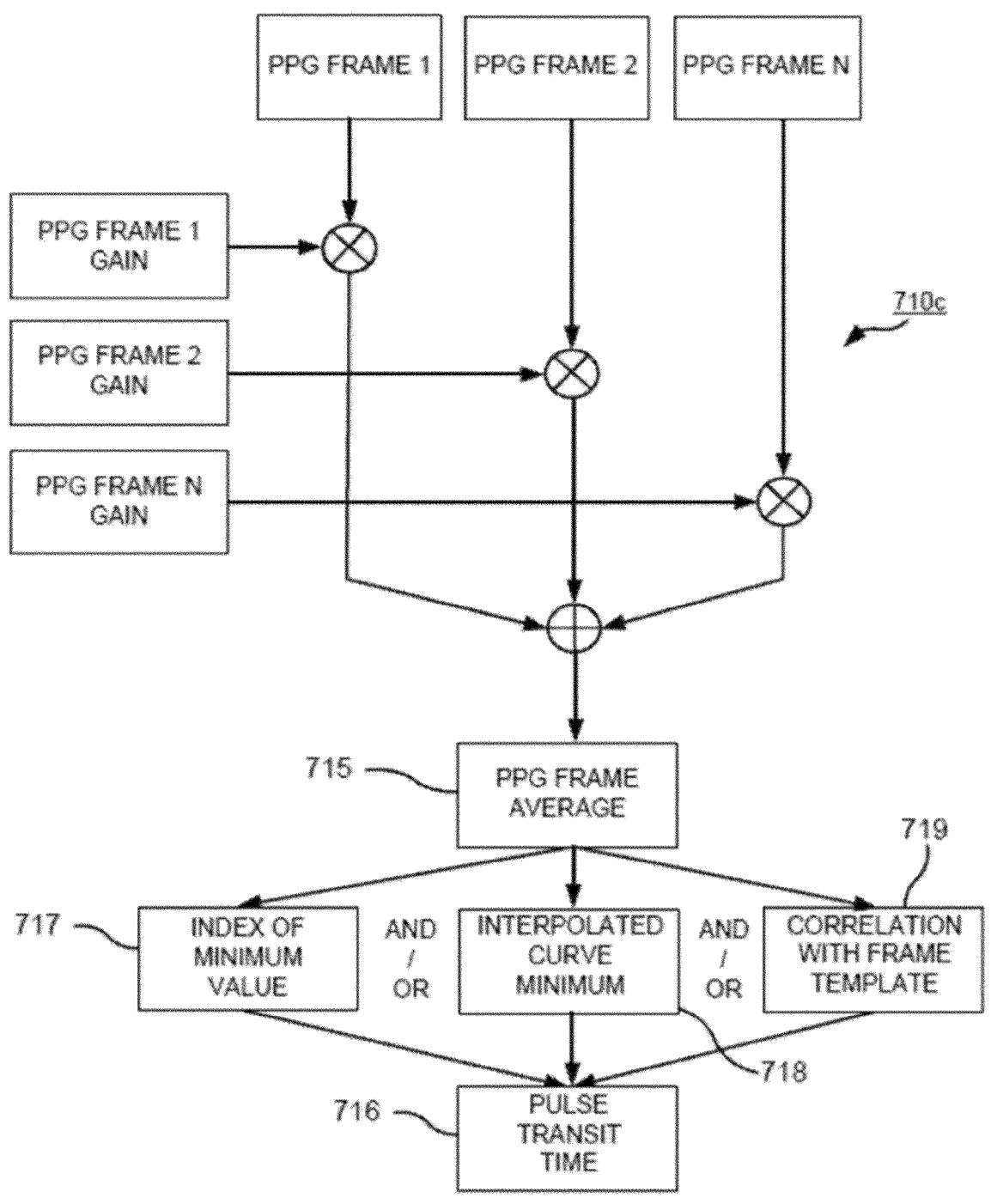

An exemplar methodology or algorithm herefor is described here and shown in the drawing FIGS. 7A, 7B and 7C. Initially, such a method 710 (which includes and/or is defined by parts 710*a*, 710*b* and/or 710*c*) takes at least one heartbeat (typical ECG) signal 712 and at least one PPG signal 711 as input as shown in FIG. 7A, e.g. The heartbeat timing information/signal 712 is used to generate heartbeat timing information by detecting the R-wave or other ECG feature from each beat; multiple ECG signals (i.e., different leads from locations on the body) may be used to obtain a better estimate of the heartbeat timing information. The PPG signal(s) 711 may use a single light wavelength or signals from multiple light wavelengths. Using the corresponding heartbeat timing information related to each PPG signal(s) 711, each PPG signal(s) 711 is segmented into "frames", see PPG Frame 1, PPG Frame 2 and PPG Frame N in FIG. 7A, where each frame contains the PPG signal of a single wavelength for the duration of one corresponding beat of the heart.

Optionally, but, typically, a PPG signal quality estimate may also be performed. An example of this is shown as method part 710*b* in FIG. 7B. This estimate may consider the variance of the PPG signal, the estimated signal-to-noise ratio of the PPG signal, PPG signal saturation, patient motion information from an accelerometer or gyroscope, an ECG or impedance measurement noise estimate, or other information about the PPG signal quality. Shown in FIG. 7B is an exemplar using accelerometer signal 713 in conjunction with PPG signal 711 to generate a PPG Signal Quality Value/Estimate 714. This signal quality estimate 714 may then be used in conjunction with the heartbeat timing information 712 to generate the gain for each "frame", see PPG Frame 1 Gain, PPG Frame 2 Gain and PPG Frame N Gain in FIG. 7B, where lower signal quality results in a lower gain. To reduce computation time, the signal quality estimate 714 may be omitted and a constant may be used for the gain information.

As shown in FIG. 7C, the gain information (PPG Frame 1 Gain, PPG Frame 2 Gain and PPG Frame N Gain from FIG. 7B) may be used (here shown as combined/manipulated) with the frame information (PPG Frame 1, PPG Frame 2 and PPG Frame N from FIG. 7A) to create a weighted, n-sample moving-average frame 715, where the PPG signal that is correlated with the heartbeat timing is reinforced while the uncorrelated noise is reduced. The number of samples included in the frame (n) 715 may be adapted to reduce noise or decrease response time. The frames may be additionally weighted by time in order to increase the contribution of recent or near-future frames with respect to frames that are further away and potentially less-relevant. This additional weighting by time may be implemented using an IIR (Infinite Impulse Response) or FIR (Finite Impulse Response) filter.

Once the average frame 715 has been produced for a given instant in time, the pulse transit time 716 may be determined by finding the shift in the frame signal with respect to the heartbeat. This may be done simply by finding the sample index 717 where the signal is at a minimum or maximum and comparing it with the frame boundary (heartbeat timing) to determine the pulse transit time. For a more precise result, the signal may be interpolated 718 using a spline or polynomial fit around the minimum or maximum values, allowing the minimum or maximum to be determined with greater precision than the sample rate. Finally, the frame may be compared 719 to a reference frame template, where the average frame is shifted with respect to the template. The shift with the highest correlation between the average frame and the template indicates the transit time 716. This reference template may be a predetermined signal, or it may be allowed to adapt by using a long-term frame average with a known transit time.

Note, such methodologies may be used with PPG and heartbeat timing information obtained from a variety of sources, including but not limited to conventional and/or to-be-developed technologies; or, may be obtained one or the other alone or together and/or together with quality signal (PPG variance, estimated PPG signal-to-noise ratio, PPG signal saturation, patient motion accelerometer or gyroscope data, an ECG or impedance measurement noise estimate, or other information about the PPG signal quality) obtained from a wearable device and/or system as described further hereinbelow.

The invention claimed is:

1. A pulse oximetry method comprising:

Placing a photoplethysmography sensor on a body of a patient;

Determining a photoplethysmogram with contribution of venous capillaries lower than 25%;

Determining arterial pulses in the photoplethysmogram; and

Determining peripheral oxygen saturation using a Ratio of Ratios method, wherein the photoplethysmography sensor is placed on a substrate intended to be adhered on a skin of the patient and protrudes from the substrate by a thickness greater than 0.1 mm.

2. The pulse oximetry method according to claim 1, wherein determining the photoplethysmogram with contribution of venous capillaries lower than 25% comprises:

Determining an electrocardiogram in time concordance with the photoplethysmogram;

Detecting a QRS complex of successive heart beats in said electrocardiogram;

Defining a succession of frames of the photoplethysmogram for a time interval between two adjacent heart beats; and Aggregating two or more of these frames together at each point in time to create a photoplethysmogram for the time interval in which contribution of venous capillaries is lower than 25%.

3. The pulse oximetry method according to claim 2, further comprising:

Determining Pulse Transit Time from a time concordant electrocardiogram and photoplethysmogram for each heart beat;

Computing a standard deviation of Pulse Transit Time over a period comprising between 10 and 45 heart beats; and Determining a confidence level of a peripheral oxygen saturation determination from the standard deviation of Pulse Transit Time.

4. The pulse oximetry method according to claim 2, wherein two or more photoplethysmography waveforms of different wavelengths are determined.

5. The pulse oximetry method according to any one of claim 2, wherein a constant component and a primary periodic component of said photoplethysmogram are determined.

6. The pulse oximetry method according to any one of claim 2, wherein defining the succession of frames includes defining intervals of said photoplethysmogram based on characteristics of said electrocardiogram and averaging values of said photoplethysmogram over a plurality of such intervals.

7. The pulse oximetry method according to claim 5, wherein said constant component and said primary periodic component of said photoplethysmogram are determined from said average values.

8. The pulse oximetry method according to claim 6, wherein said electrocardiogram includes R wave signals each with a peak value in each of said heart beats and said intervals are determined with respect to the peak values of the R wave signals.

9. A pulse oximeter comprising a photoplethysmography sensor and an ECG sensor, said pulse oximeter being suitable to implement the pulse oximetry method according to claim 2.

10. The pulse oximetry method according to claim 1, wherein the photoplethysmography sensor comprises an optical lens surrounded by an adhesive layer and wherein the optical lens is protruding, so as to maintain pressure great enough, to compress only the venous capillaries.

11. The pulse oximetry method according to claim 1, wherein the photoplethysmography sensor protrudes from the substrate by a thickness greater than 0.5 mm.

12. The pulse oximetry method according to claim 1, wherein the photoplethysmography sensor is placed on a back of the patient.

13. The pulse oximetry method according to claim 12, wherein the photoplethysmography sensor is placed near a nape region of a neck of the patient.

14. The pulse oximetry method according to claim 12, wherein the photoplethysmography sensor is placed on a vertebra.

15. The pulse oximetry method according to claim 12, wherein the photoplethysmography sensor is placed on a T1 vertebra.

* * * * *